US012802315B2

(12) United States Patent
Takanashi et al.

(10) Patent No.: US 12,802,315 B2
(45) Date of Patent: Nov. 17, 2026

(54) TECHNIQUE FOR DETERMINING AN OPERATING PARAMETER OF A TOMOGRAPHIC IMAGING SYSTEM

(71) Applicant: RIKEN, Saitama (JP)

(72) Inventors: Takaoki Takanashi, Saitama (JP); Shigeho Noda, Saitama (JP); Masaru Tamura, Saitama (JP); Yoshie Otake, Saitama (JP)

(73) Assignee: Riken, Saitama (JP)

( * ) Notice: Subject to any disclaimer, the term of this patent is extended or adjusted under 35 U.S.C. 154(b) by 289 days.

(21) Appl. No.: 18/262,230

(22) PCT Filed: Jan. 21, 2022

(86) PCT No.: PCT/JP2022/002247
§ 371 (c)(1),
(2) Date: Nov. 22, 2023

(87) PCT Pub. No.: WO2022/158575
PCT Pub. Date: Jul. 28, 2022

(65) Prior Publication Data

US 2024/0153162 A1 May 9, 2024

(30) Foreign Application Priority Data

Jan. 21, 2021 (JP) ................................ 2021-008321

(51) Int. Cl.
*G06T 12/20* (2026.01)
*A61B 6/00* (2024.01)
(Continued)

(52) U.S. Cl.
CPC ................ *G06T 12/20* (2026.01); *A61B 6/03* (2013.01); *A61B 6/5205* (2013.01);
(Continued)

(58) Field of Classification Search
CPC ......... G06T 12/00; G06T 12/10; G06T 12/20; G06T 12/30; G06T 2211/40;
(Continued)

(56) References Cited

U.S. PATENT DOCUMENTS 5,778,038 A * 7/1998 Brandt .................. G06T 11/008 378/4
9,996,951 B2 * 6/2018 Sijbers .................. G06T 11/006
(Continued)

FOREIGN PATENT DOCUMENTS

CN 104899827 A 9/2015
JP 2015-226753 A 12/2015
(Continued)

OTHER PUBLICATIONS

Aviash C. Kak and Molcolm Slaney, “Principles of Computerized Tomographic Imaging,” IEEE Press (1988).
(Continued)

*Primary Examiner* — Scott A Rogers
(74) *Attorney, Agent, or Firm* — McDonnell Boehnen Hulbert & Berghoff LLP

(57) ABSTRACT

To provide a system, a method, and a program whereby a reconstructed image supported by an algebraically exact solution of an inverse discrete Radon transform can be generated using fewer computational resources, and a recording medium in which the program is recorded. A computer-implemented method for determining an operating parameter of a tomographic imaging system for reconstructing a tomographic image by an inverse discrete Radon transform in a scan angle range of less than (180°-180°/number of projections), wherein the method includes: a step for determining a system matrix on the basis of the value of one or two operating parameters designated from among a number of detection elements, a number of projections, and
(Continued)

a scan angle range less than (180°-180°/number of projections); a step for generating a square system matrix from the determined system matrix; a step for deciding whether an inverse matrix exists for the square system matrix; and a step for repeating said steps as necessary to determine the value of an operating parameter that corresponds to an operating parameter other than the designated one or two operating parameters, for which the inverse matrix of the square system matrix exists.

9 Claims, 22 Drawing Sheets

(51) Int. Cl.
*A61B 6/03* (2006.01)
*G01N 23/046* (2018.01)
*G06F 17/16* (2006.01)

(52) U.S. Cl.
CPC ........... *G01N 23/046* (2013.01); *G06F 17/16* (2013.01); *G01N 2223/419* (2013.01); *G06T 2211/424* (2013.01); *G06T 2211/436* (2013.01)

(58) Field of Classification Search
CPC ......... G06T 2211/424; G06T 2211/436; G06T 11/003; G06T 11/006; G06F 17/16; A61B 6/03; A61B 6/5205; G01N 23/046; G06N 2223/419
See application file for complete search history.

(56) References Cited

U.S. PATENT DOCUMENTS

| | | | | |
|---|---|---|---|---|
| 11,307,153 | B2 * | 4/2022 | Takanashi | G01N 23/046 |
| 11,375,964 | B2 * | 7/2022 | Kanda | G06T 11/008 |
| 12,394,117 | B2 * | 8/2025 | Yan | G06T 11/006 |
| 2009/0123048 | A1 | 5/2009 | Leroux | |
| 2013/0177225 | A1 | 7/2013 | Zamyatin | |
| 2014/0029819 | A1 | 1/2014 | Zeng | |
| 2020/0402274 | A1 | 12/2020 | Liu | |
| 2021/0228167 | A1 | 7/2021 | Kanda | |
| 2021/0262947 | A1 | 8/2021 | Takanashi | |
| 2024/0185488 | A1 * | 6/2024 | Yan | G06T 11/005 |
| 2025/0082294 | A1 * | 3/2025 | Okubo | A61B 6/463 |

FOREIGN PATENT DOCUMENTS

| | | | |
|---|---|---|---|
| WO | 2013105583 | A1 | 7/2013 |
| WO | 2014021349 | A1 | 2/2014 |
| WO | 2019230740 | A1 | 12/2019 |
| WO | 2019230741 | A1 | 12/2019 |

OTHER PUBLICATIONS

Stanley R. Deans, “The Radon Transform and Some of Its Applications,” Krieger Publications (1983).
Robert L. Siddon, “Fast calculation of the exact radiological path for a three-dimensional CT array,” Medical Physics, vol. 12, No. 2, pp. 252-255 (1985).
Sunnegardh, J. and Danielsson, P.-E. “A New Anti-Aliased Projection Operator for Iterative CT Reconstruction,” 9 th International Meeting of Fully Three-Dimensional Image Reconstruction in Radiology and Nuclear Medicine, pp. 125-127 (2009).
Serhan O. Isikman, Waheb Bishara, Sam Mavandadi, Frank W. Yu, Steve Feng, Randy Lau, and Aydogan Ozcan “Lens-free optical tomographic microscope with a large imaging volume on a chip” PNAS May 3, 2011 108 (18) 7296-7301; https://doi.org/10.1073/pnas.1015638108.
N. Kawase, M. Kato, H. Nishioka, H. Jinnai, Ultramicroscopy, 107, 8-15 (2007) “Transmission electron microtomography without the “missing wedge” for quantitative structural analysis”.
International Search Report for corresponding PCT application No. PCT/JP2022/002247, dated Apr. 5, 2022.
Zhang, Lingli et al., “A Regularized Limited-Angle CT Reconstruction Mode Based on Sparse Multi-level Information Groups of the images,” Image and Graphics Technologies and Applications (2021), pp. 267-282. DOI:10.1007/978-981-16-7189-0_21.

* cited by examiner $$\begin{pmatrix} p_1 \\ p_2 \\ p_3 \\ p_4 \\ p_5 \\ p_6 \\ p_7 \\ p_8 \\ p_9 \\ p_{10} \\ p_{11} \\ p_{12} \\ p_{13} \\ p_{14} \\ p_{15} \\ p_{16} \end{pmatrix} = \begin{pmatrix} 1 & 0 & 1 & 0 \\ 1 & 0 & 1 & 0 \\ 0 & 1 & 0 & 1 \\ 0 & 1 & 0 & 1 \\ 1 & 0 & 1 & 0 \\ 1 & 1 & 1 & 0 \\ 0 & 1 & 1 & 1 \\ 0 & 1 & 0 & 1 \\ 1 & 0 & 1 & 0 \\ 1 & 1 & 1 & 0 \\ 0 & 1 & 1 & 1 \\ 0 & 1 & 0 & 1 \\ 1 & 1 & 0 & 0 \\ 1 & 1 & 1 & 0 \\ 0 & 1 & 1 & 1 \\ 0 & 0 & 1 & 1 \end{pmatrix} \begin{pmatrix} a_1 \\ a_2 \\ a_3 \\ a_4 \end{pmatrix}$$

FIG. 18

$$\begin{pmatrix} p_1 \\ p_2 \\ p_3 \\ p_4 \\ p_5 \\ p_6 \\ p_7 \\ p_8 \end{pmatrix} = \begin{pmatrix} 1 & 0 & 1 & 0 \\ 1 & 0 & 1 & 0 \\ 0 & 1 & 0 & 1 \\ 0 & 1 & 0 & 1 \\ 1 & 0 & 1 & 0 \\ 1 & 1 & 1 & 0 \\ 0 & 1 & 1 & 1 \\ 0 & 1 & 0 & 1 \end{pmatrix} \begin{pmatrix} a_1 \\ a_2 \\ a_3 \\ a_4 \end{pmatrix}$$

FIG. 19

$$\begin{pmatrix} p_1 \\ p_2 \\ p_3 \\ p_4 \\ p_5 \\ p_6 \\ p_7 \\ p_8 \\ p_9 \\ p_{10} \\ p_{11} \\ p_{12} \end{pmatrix} = \begin{pmatrix} 1 & 0 & 1 & 0 \\ 0 & 1 & 0 & 1 \\ 1 & 0 & 1 & 0 \\ 0 & 1 & 0 & 1 \\ 1 & 0 & 1 & 0 \\ 0 & 1 & 0 & 1 \\ 1 & 1 & 1 & 0 \\ 0 & 1 & 1 & 1 \\ 1 & 1 & 1 & 0 \\ 0 & 1 & 1 & 1 \\ 1 & 1 & 0 & 0 \\ 0 & 0 & 1 & 1 \end{pmatrix} \begin{pmatrix} a_1 \\ a_2 \\ a_3 \\ a_4 \end{pmatrix}$$

FIG. 20

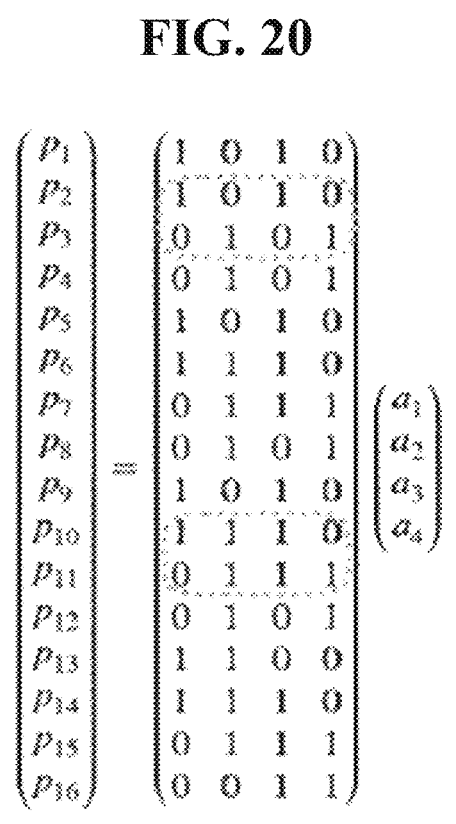

$$
\begin{pmatrix} p_1 \\ p_2 \\ p_3 \\ p_4 \\ p_5 \\ p_6 \\ p_7 \\ p_8 \\ p_9 \\ p_{10} \\ p_{11} \\ p_{12} \\ p_{13} \\ p_{14} \\ p_{15} \\ p_{16} \end{pmatrix}
=
\begin{pmatrix}
1 & 0 & 1 & 0 \\
1 & 0 & 1 & 0 \\
0 & 1 & 0 & 1 \\
0 & 1 & 0 & 1 \\
1 & 0 & 1 & 0 \\
1 & 1 & 1 & 0 \\
0 & 1 & 1 & 1 \\
0 & 1 & 0 & 1 \\
1 & 0 & 1 & 0 \\
1 & 1 & 1 & 0 \\
0 & 1 & 1 & 1 \\
0 & 1 & 0 & 1 \\
1 & 1 & 0 & 0 \\
1 & 1 & 1 & 0 \\
0 & 1 & 1 & 1 \\
0 & 0 & 1 & 1
\end{pmatrix}
\begin{pmatrix} a_1 \\ a_2 \\ a_3 \\ a_4 \end{pmatrix}
$$

TECHNIQUE FOR DETERMINING AN OPERATING PARAMETER OF A TOMOGRAPHIC IMAGING SYSTEM

TECHNICAL FIELD

The present invention relates to a system, a method, and a program for tomographic imaging, and a recording medium in which the program is recorded.

BACKGROUND ART

Tomographic imaging method (tomography) using transmitting electromagnetic waves or particle beams such as X-rays, gamma rays, and light waves, or waves or particles exhibiting any sort of permeability or transmission ability such as seismic waves or others have been put into practical use. Typical examples include an X-ray CT scanner, SPECT (Single Photon Emission Computed Tomography), Optical Tomography, and Transmission Electron Microtomography (TEMT) used in medical and industrial applications. A mathematical principle assuring that the tomographic image of an object is obtainable by these imaging methods is the Radon transform. In this context, the process for externally capturing the attenuation rate of each part inside the object as imaging information is described by the Radon transform, and the process for reconstructing the tomographic information of the object from the information externally captured is described by the inverse Radon transform. That is, the operation for detecting the flow of the transmitted waves or particles attenuated by the object at each position by changing the irradiation direction or the detection direction corresponds to the Radon transform. In contrast, an operation for reconstructing an image by estimating the attenuation rate of each part inside the object from the intensity information of each direction and each position of the detection corresponds to the inverse Radon transform. The Radon- or inverse Radon transform for continuous coordinates and continuous directions for real images is carried out using sampling points on coordinates or orientations for handling a finite number of pixels. The inverse Radon transform (inverse discrete Radon transform) for image reconstruction under sampled coordinates and orientations is reduced into solving multiple simultaneous linear equations; in other words matrix operations. These mathematical aspects are described in standard textbooks (e.g., Non-Patent Documents 1 and 2).

A technique in which noise and artifacts are further reduced by means of the iterative approximation method where iterative processing takes place (iterative reconstruction, IR), has also attracted attention. The iteration process is repeated, for example, 100 times or more to obtain the solution. Such a technique for obtaining a reconstructed image by deriving an approximate solution of multiple simultaneous linear equations by relying on an algebraic approach is called an ART (Algebraic Reconstruction Technique). The ARTs include techniques that are referred to as, for example, Maximum Likelihood-Expectation Maximization (ML-EM), Additive-Simultaneous Iterative Reconstruction Techniques (ASIRT), and Multiplicative-Simultaneous Iterative Reconstruction Techniques (MSIRT). In conventional ARTs, a calculation scale becomes huge and a large amount of computational resources are required. In addition, repeated iterations often do not approach the solution corresponding to the true image and are captured by the local solution. In contrast, approximation calculation efficiency in computing has been improved without resorting to algebraic approaches while methods utilizing realistic calculation resources have also been sought out. Such examples include FBP (Filtered Back Projection) (for example, Patent Document 1). Since the scale of the FBP calculation is smaller than that of algebraic approaches, it is currently most frequently used with X-ray CT scanners.

In the course of the development progress of the tomographic imaging methods from the beginning until today, there has been a continuing demand for increasing the number of imaging pixels, and therefore the possibility of the FBP has been intensively studied. The FBP is, however, generally disadvantageous in the quality of reconstructed images in which various artifacts readily appear compared to IR. Nowadays, the ARTs, which are intrinsically advantageous in the quality of a reconstructed image, have attracted much attention again based on continuing development of computational power (see, for example, Patent Document 2).

CITATION LIST

Patent Documents

Patent Document 1: WO 2014/021349
Patent Document 2: WO 2013/105583

Non-Patent Documents

Non-Patent Document 1: Aviash C. Kak and Molcolm Slaney, "Principles of Computerized Tomographic Imaging", IEEE Press (1988)
Non-Patent Document 2: Stanley R. Deans, "The Radon Transform and Some of its Applications", Krieger Publications (1983)
Non-Patent Document 3: Robert L. Siddon, "Fast calculation of the exact radiological path for a three-dimensional CT array", Medical Physics, vol. 12, no. 2, pages 252-255 (1985)
Non-Patent Document 4: Sunnegardh, J. and Danielsson, P.-E. "A New Anti-Aliased Projection Operator for Iterative CT Reconstruction", 9$^{th}$ International Meeting of Fully Three-Dimensional Image Reconstruction in Radiology and Nuclear Medicine, pages 125-127 (2009)
Non-Patent Document 5: Serhan O. Isikam, Waheb Bishara, Sam Mavandadi, Frank W. Yu, Steve Feng, Randy Lau, and Aydogan Ozcan "Lens-free optical tomographic microscope with a large imaging volume on a chip", PNAS May 3 2011, 108 (18) 7296-7301; https://doi.org/10.1073/pnas.1015638108
Non-Patent Document 6: N. Kawase, M. Kato, H. Nishioka, H. Jinnai, Ultramicroscopy, 107, 8-15 (2007), "Transmission electron microtomography without the "missing wedge" for quantitative structural analysis"

SUMMARY OF INVENTION

Technical Problem

The ARTs allow the high quality of reconstructed images as described above. However, even when a conventional ART is employed in a situation in which the number of imaging pixels is increased, the number of dimensions (or variables to be determined) of the simultaneous linear equation to be solved is increased, which requires a huge scale of computational resources and takes a long time for processing.

The tomographic imaging method generally requires a scan angle range of 180°, but neither Transmission Electron Microtomography (TEMT) nor an optical CT microscope can ensure the scan angle range of 180°. For example, the optical CT microscope disclosed in Non-patent Document 5 ensures at most a scan angle range of 100°, and the TEMT disclosed in Non-patent Document 6 ensures at most a scan angle range of 160°.

Thus, one of the objects of the present invention is to provide a system, a method, and a program that can generate a reconstructed image supported by an algebraic exact solution of the inverse discrete Radon transform using fewer computational resources, and to provide a recording medium in which the program is recorded.

Moreover, one of the objects of the present invention is to provide a system, a method, and a program that can generate a reconstructed image supported by an algebraic exact solution of an inverse discrete Radon transform using fewer computational resources in a scan angle range of less than (180°-180°/number of projections), and to provide a recording medium in which the program is recorded.

Solution to Problem

One aspect of the present invention provides a computer-implemented method for determining an operating parameter of a tomographic imaging system for reconstructing a tomographic image by an inverse discrete Radon transform in a scan angle range of less than (180°-180°/number of projections), including: a step for determining a system matrix on the basis of the values of one or two operating parameters designated from among a number of detection elements, a number of projections, and a scan angle range of less than (180°-180°/number of projections); a step for generating a square system matrix from the determined system matrix; a step for deciding whether an inverse matrix exists for the square system matrix; and a step for repeating each of said steps as necessary to determine the value of an operating parameter that corresponds to an operating parameter other than the designated one or two operating parameters for which the inverse matrix of the square system matrix exists.

The step for generating a square system matrix may be a step that first removes elements of overlapping row- or column vectors from the determined system matrix to generate a square system matrix.

The step for generating a square system matrix may be a step that first removes elements of overlapping row- or column vectors from the determined system matrix, and subsequently removes row- or column vectors randomly for elements of the remaining row- or column vectors to generate a square system matrix.

One aspect of the present invention provides a program for causing a computer to perform the above method.

One aspect of the present invention provides a computer-readable recording medium in which the program is recorded.

One aspect of the present invention provides a device for determining an operating parameter of a tomographic imaging system for reconstructing a tomographic image by an inverse discrete Radon transform in a scan angle range of less than (180°-180°/number of projections), including: a system matrix determination unit for determining a system matrix on the basis of the values of one or two operating parameters designated from among a number of detection elements, a number of projections, and a scan angle range of less than (180°-180°/number of projections); a square system matrix generation unit for generating a square system matrix from the system matrix; and an inverse matrix decision unit for deciding whether an inverse matrix exists for the square system matrix, said device repeating, as necessary, the system matrix determination, the square system matrix generation, and the decision on whether the inverse matrix exists, to determine the value of an operating parameter that corresponds to an operating parameter other than the designated one or two operating parameters for which the inverse matrix of the square system matrix exists.

The square system matrix generation unit may be a unit which first removes elements of overlapping row- or column vectors from the determined system matrix to generate a square system matrix.

The square system matrix generation unit may be a unit which first removes elements of overlapping row- or column vectors from the determined system matrix, and subsequently removes row- or column vectors randomly for the elements of the remaining row- or column vectors to generate a square system matrix.

One aspect of the present invention provides a computer-implemented method for determining an operating parameter of a tomographic imaging system for reconstructing a tomographic image by an inverse discrete Radon transform in a scan angle range of a predetermined value being less than 180°, including: a step for determining a system matrix on the basis of the values of one or two operating parameters designated from among a number of detection elements, a number of projections, and a scan angle range of a predetermined value being less than 180°; a step for generating a square system matrix from the system matrix; a step for deciding whether an inverse matrix exists for the square system matrix; and a step for repeating each of said steps as necessary to determine the value of an operating parameter that corresponds to an operating parameter other than the designated one or two operating parameters for which the inverse matrix of the square system matrix exists.

One aspect of the present invention provides a device for determining an operating parameter of a tomographic imaging system for reconstructing a tomographic image by an inverse discrete Radon transform in a scan angle range of a predetermined value of less than 180°, including: a system matrix determination unit for determining a system matrix on the basis of the values of one or two operating parameters designated from among a number of detection elements, a number of projections, and a scan angle range of a predetermined value being less than 180°; a square system matrix generation unit for generating a square system matrix from the system matrix; and an inverse matrix decision unit for deciding whether an inverse matrix exists for the square system matrix, the device repeating as necessary the system matrix determination, the square system matrix generation, and the decision on whether the inverse matrix exists, to determine the value of an operating parameter that corresponds to an operating parameter other than the designated one or two operating parameters for which the inverse matrix of the square system matrix exists.

The present specification and claims may use terminology that follows the conventions of the art to which the disclosure belongs unless it renders the description unclear. Waves may include any sort of wave that can be conceived of as attenuated through propagation, such as electromagnetic waves and sound waves, and may include light waves (infrared, visible, and ultraviolet) and oscillations (e.g., seismic waves). Particles include any sort of particles that can be conceived of as attenuated through propagation in a stream of particle rays, including neutron rays and other radiation as well. Anything that may have properties both of wave and particle in a quantum mechanical sense, such as electrons and photons, is also included in either or both of the waves or particles. Similarly, anything that is regarded as waves or particles in a classical mechanics point of view is also included in one or both of the waves or particles. These waves or particles can be used in the practice of the present disclosure, even if they are generated by a device (or an emitting device) that is an artificial source of their emission, or if they are generated from natural sources, for example, cosmic rays, or if they are generated due to a property of the object, for example, radiation emitted from various parts of the object (which are referred to as "waves or particles that are not generated by the emitting device" in this application).

When scanning in an angle range of 180°, the captured image at a scan angle of 0° is identical with the captured image at a scan angle of 180°, so that the expression "a scan angle range of 180°" is conventionally used as an expression meaning a scan angle range of from a scan starting angle of 0° to a scan end angle of (180°-180°/number of projections). Thus, in the present specification and claims, a scan angle range smaller than the conventionally-expressed "scan angle range of 180°" is expressed as "a scan angle range of less than (180°-180°/number of projections)".

Advantageous Effects of Invention

The present invention having the above features can provide a system, a receiving device, a transmitting device, a method, and a program that can generate a reconstructed image supported by an algebraic exact solution of an inverse discrete Radon transform using fewer computational resources, and can provide a recording medium in which the program is recorded.

In addition, the present invention having the above features can provide a system, a method, and a program that can generate a reconstructed image supported by an algebraic exact solution of an inverse discrete Radon transform in a scan angle range of less than (180°-180°/number of projections) using fewer computational resources, and can provide a recording medium in which the program is recorded.

BRIEF DESCRIPTION OF DRAWINGS

FIG. 18 is a diagram showing Formula (6) in the form of a matrix.

FIG. 19 is a diagram showing Formula (10) in the form of a matrix.

FIG. 20 is a diagram showing Formula (14) in the form of a matrix.

DESCRIPTION OF EMBODIMENTS (Principle)

Figure 1A:
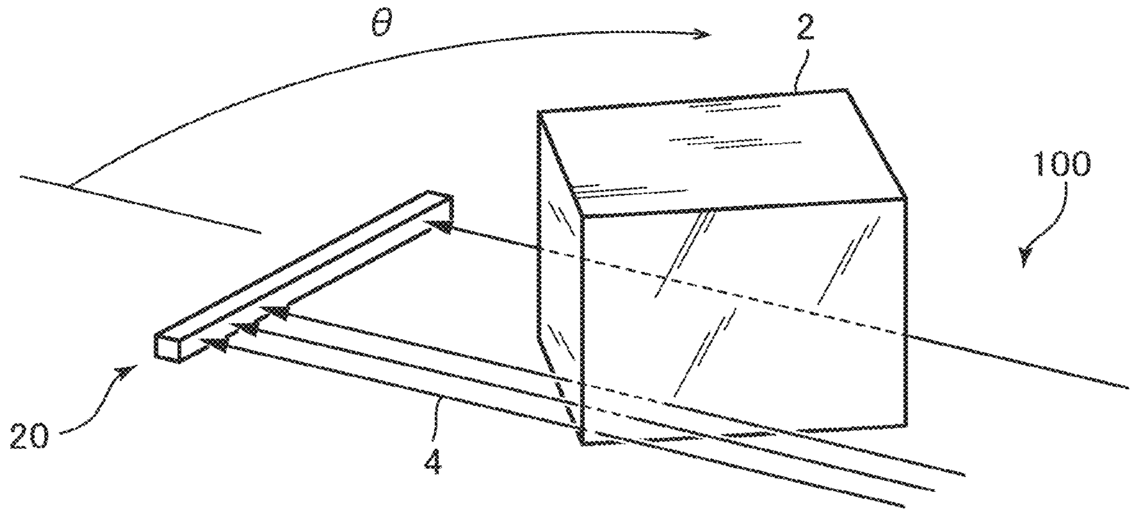
FIG. 1A is a perspective diagram showing a relationship between an object to be imaged and a detection device in an example of a tomographic imaging system according to an embodiment of the present invention.

First, the principle of tomographic imaging of the present disclosure is described by referring to FIGS. 1A to 7. An exemplary geometrical arrangement of the present embodiment is described. FIG. 1A is a perspective diagram showing a relationship between an object 2 to be imaged and a detection device 20 in an example of a tomographic imaging system 100 according to the present embodiment. FIG. 1B is a schematic diagram for explaining a schematic configuration including a plane arrangement on a cut surface of the object 2 to be imaged in an example of the tomographic imaging system 100 according to the present embodiment. On one plane of this space, a group of pixels having N×N pixels constituting a tomographic image is defined, and the integer N is referred to as a resolution. In a conventional method, the integer N is matched with the number of detection elements 22 of the detection device 20. A beam 4 of waves or particles is included in the plane and is emitted from an emission device 10. The detection device 20 and the emission device 10 are rotatable in relation to the object 2 while the relative arrangement is fixed. For the operation of the device including such control, the tomographic imaging system 100 has a control unit 501 described later. The rotation is relative to the above group of pixels and the object 2. Thus, the detection device 20 and the emission device 10 alone are not always rotated; instead, it may also be possible that the detection device 20 and the emission device 10 are fixed on an installation floor surface (not shown), and the object 2 is rotated together with the group of pixels.

Figure 1B:
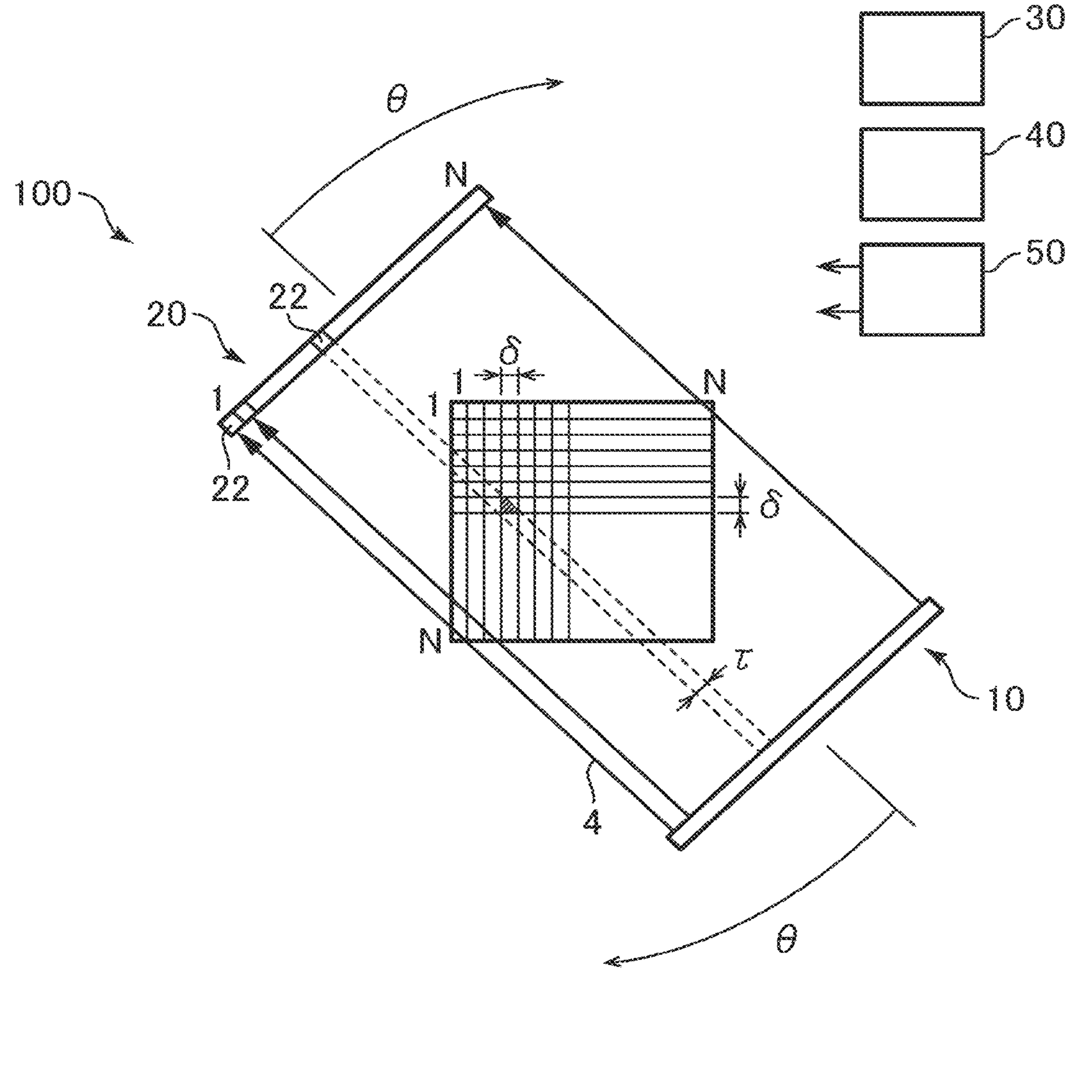
FIG. 1B is a schematic diagram for explaining a schematic configuration including a plane arrangement on a cut surface of an object to be imaged in an example of a tomographic imaging system according to an embodiment of the present invention, where FIG. 1B also shows the entire configuration of the tomographic imaging system according to an embodiment of the present invention.

The operation for irradiating the beam 4 of waves or particles by the emission device 10 and detecting the beam 4 on the opposite side of the object 2 by the detection device 20 in conventional methods uses sampling by intervals in which the scanning range in the detection direction θ is divided by the pixel number N. The number of the sampling in the detection direction is hereinafter also referred to as "the number of projections". The scanning range in the detection direction θ is ordinarily 0° to 180°, in other words the scan angle range φ is 180°, with the parallel beams 4 as shown in FIG. 1B; conventional methods use a (180/N)° interval in sampling the detection signal from the detection device 20. The typical scanning operation in the detection direction θ of the tomographic imaging system 100, including the present embodiment, is performed with sampling by electrically controlling the timings of acquiring values of the detection device 20 while performing constant-speed rotation, in which the angle of detection direction θ is increased or decreased at a constant speed. However, the present embodiment is not limited to such an operation.

Figure 2:
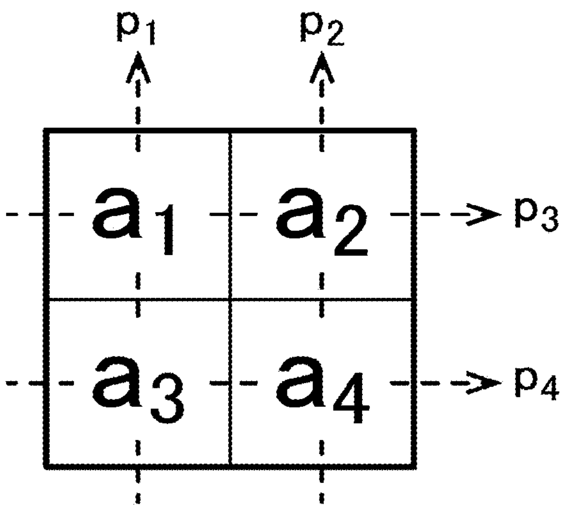
FIG. 2 is an explanatory diagram for explaining a principle of a conventional algebraic approach of an inverse discrete Radon transform.

FIG. 2 is an explanatory diagram explaining a principle of a conventional algebraic approach of an inverse discrete Radon transform. FIG. 2 illustrates the primitive nature of the process of irradiating waves or particles and reconstructing a tomographic image using the intensity data after transmission. Each of the square areas arranged in 2 columns×2 rows as illustrated should be associated with the pixels of a tomographic image corresponding to the resolution N=2, and these squares may have four values of $a_1$ to $a_4$. These values carry the degree of beam attenuation by the object 2 at the position of each pixel and are the values to be determined. Broken line arrows passing through the plurality of pixels and changing in the direction at 180°/N, namely 90°, corresponding to the resolution N=2 correspond to the irradiation of the wave- or particle beams and the positions of the detection elements. Each numerical value pointed at by each arrow means a value (e.g., a degree of attenuation) obtained when the detection element of the detection device is positioned ahead of the arrow, and the sum of the values of the pixels with arrows having passed through is herein indicated by the numerical value. That is, the arrows represent the beams of waves or particles, and the pixels with arrows passing through and the directions of the arrows indicate the irradiation and detection (hereinafter simply referred to as "irradiation"). The total value pointed at by the arrow corresponds to the attenuation component detected by each detection element when the detection element of the detection device is positioned ahead of the arrow. Determining the four values of $a_1$ to $a_4$ only by values pointed at by the arrows, namely values obtained from the detection device, corresponds to a process of executing an inverse discrete Radon transform on the basis of the values indicated by the detection elements of the detection device for reconstructing the tomographic image.

In the example shown in FIG. 2, the connections by each of the arrows in $a_1$ to $a_4$ provide linear sums, which can be rewritten into the following simultaneous equations.

[Math 1]

$$
\begin{aligned}
p_1 &= a_1 + a_3 \\
p_2 &= a_2 + a_4 \\
p_a &= a_3 + a_4 \\
p_4 &= a_1 + a_2
\end{aligned}
\tag{1}
$$

Here, to illustrate the case of X-ray CT, $p_1$ to $p_4$ are the values measured at each pixel and in each detection direction of the X-ray in FIG. 2, and $a_1$ to $a_4$ are X-ray absorption coefficients. Such simultaneous equations cannot have a unique value. Here, even if new $a'_1$ to $a'_4$ which were shifted using a given number A were substituted as described below:

[Math 2]

$$\begin{aligned} a_1 &\to a_1' = a_1 + A \\ a_2 &\to a_2' = a_2 - A \\ a_3 &\to a_3' = a_3 - A \\ a_4 &\to a_4' = a_4 + A \end{aligned} \tag{2}$$

Formula (1) would remain invariant. That is, while Formula (1) has four dimensions (i.e., variables to be determined), the substantial number of the simultaneous equations that can be derived by the detections indicated by the arrows is three. In this context, all four values of $a_1$ to $a_4$ are indeterminate and cannot be determined.

Organizing this relationship by another mathematical relationship, the above Formula (1) is represented in a matrix form more generally as

[Math 3]

$$\begin{pmatrix} p_1 \\ p_2 \\ p_3 \\ p_4 \end{pmatrix} = \begin{pmatrix} 1 & 0 & 1 & 0 \\ 0 & 1 & 0 & 1 \\ 0 & 0 & 1 & 1 \\ 1 & 1 & 0 & 0 \end{pmatrix} \begin{pmatrix} a_1 \\ a_2 \\ a_3 \\ a_4 \end{pmatrix} \leftrightarrow a_n = \sum_m w_{nm} a_m , \tag{3}$$

in which $w_{nm}$ represents elements of a matrix W which is a square matrix of $N^2$ rows×$N^2$ columns (hereinafter referred to as "system matrix"). In general, whether the matrix W has an inverse matrix $W^{-1}$ can be determined by various mathematical methods such as rank value-based determination. That is, the fact that the matrix W has an inverse matrix is equivalent to the fact that the rank value of the square matrix W having $N^2$ rows×$N^2$ columns (rank($w_{nm}$)) attains N×N. If the matrix W has an inverse matrix, the simultaneous equations corresponding to Formula (3) can be uniquely solved. In the above matrix represented by Formula (3), the rank value (rank($w_{nm}$)) is calculated to be 3<4, which does not attain the value that is necessary to have an inverse matrix.

In contrast, when the matrix W has an inverse matrix $W^{-1}$, the values of $a_1$ to $a_4$ can be obtained from the values of $p_1$ to $p_4$. In other words, the values of $a_1$ to $a_4$ can be uniquely determined only by an algebraically strict method of operating the inverse matrix to the measured values $p_1$ to $p_4$. This difference suggests that appropriate design in the step of irradiation would allow the obtainment of a solution through an algebraic approach even in a multiple simultaneous linear equations having a more general form for a reconstruction process of a real tomographic image, in other words there would be room for obtaining an exact solution that is not indeterminate by an algebraic approach. The present inventors found that an exact solution may be obtained even in a scan angle range of less than (180°-180°/number of projections), and further found that three operating parameters, namely a number of detection elements, a number of projections meaning a number of samples in a detection direction, and a scan angle range, may be adjusted as an appropriate design in the step of irradiation to obtain an exact solution. The present inventors also found that in this case, when a number of detection elements and a number of projections meaning a number of samples are larger than a resolution of a tomographic image, the probability of the existence of an exact solution increases, and that the larger a number of samples is than a resolution, the more the probability of the existence of an exact solution increases and simultaneously the more a range in which an exact solution exists enlarges, expanding in a direction in which a scan angle range is smaller.

FIG. 1B is referred to again. The beam 4 has a spread covering all the pixel ranges at the above coordinates, and a part directed to each detection element 22 has a width τ. The contribution of the pixel for the beam 4 related to the detection element 22 is typically the overlap of the width τ and each pixel (with vertical and horizontal lengths of δ), where the width is of the part of the beam 4 directed toward one of the detection elements 22. This overlap for one pixel is illustrated in FIG. 1B using a hatch. For all of the N×N pixels, the contribution is determined for each detection direction θ, for each detection element 22. The system matrix W holds these contributions as numerical values. Among the irradiation and the image reconstruction, the discrete Radon transform representing the irradiation is expressed as follows using the system matrix W by the multiplication operation using a matrix:

$$X' = WX \tag{4}$$

Here, the system matrix W is usually arranged in the row direction for the sampling points in the space corresponding to the total number of pixels and in the column direction for the sampling points in the irradiation and in the detection corresponding to the interval in the detection direction and the detection elements. When a conventional technique is applied to a setting such as the number of pixels in FIG. 1B, the system matrix W becomes a square matrix having N×N elements both in the row and column directions, which makes the total number of the elements to $N^4$. This is because there exist N×N pixels, N samples for the scan range of the detection direction θ, and N elements for the number of detection elements 22. It should be noted that the value N has increased over time to improve the image quality, and in a typical example, the value of N is set to approximately 1024, or $10^3$. The maximum value N is approximately 2000 in a conventional technique. However, the value of N is not particularly limited in the present embodiment. In the case where N is approximately $10^3$, the system matrix has a scale of approximately $10^6$ both in the row and column directions, and the number of elements is approximately $10^{12}$.

In Formula (4), X represents an attenuation image, which is an image representing attenuation (also including absorption and scattering) at the position of each pixel, as a column vector. Although the attenuation image in the actual space is the two-dimensional image of the N×N pixels shown in FIG. 1B, X is a vector for calculation with the system matrix W, in which the vector is obtained by vectorizing the column direction into the total number of N×N pixels. In Formula (4), a column vector X' on the left-hand side obtained by operating the system matrix W to the attenuation image X corresponds to an image called sinogram. Corresponding to the arrangement in the system matrix W, in which the sampling points along the detection direction and detection elements are associated to a column direction, the column vector X' also indicates the detection intensity obtained for each of the sampling points in the detection direction and each of the detection elements. The sinogram is obtained by rearranging the elements of the column vector X' into two-dimensions with the axis of the detection element and the axis in the detection direction interval. As described above, Formula (4) expresses irradiation and detection. In the figure shown in FIG. 2, the column vector X corresponds to each value of $a_1$ to $a_4$, the column vector X' corresponds to each value pointed at by each arrow, and the system matrix W reflects a correspondence between each arrow and each pixel.

The reconstruction of a tomographic image is a process for calculating a column vector X from a column vector X' for the sinogram and the system matrix W and obtaining an attenuation image from the column vector X, on the assumption that Formula (4) is realized. That is, the reconstruction of the tomographic image is expressed by the following formula:

$$X=W^{-1}X' \tag{5}$$

Here, $W^{-1}$ is the inverse matrix of W, and Formula (5) is obtained by operating $W^{-1}$ on both sides of Formula (4) and replacing the right and left-hand sides. In practice, a square matrix W does not always have an inverse matrix $W^{-1}$. The fact that the respective values of $a_1$ to $a_4$ are not determined in FIG. 2 means that $W^{-1}$ does not exist for such manner of irradiation and detection. Although the above description based on FIG. 1B is for irradiating a parallel beam, the present embodiment can be applicable to the emission device 10 or the detection device 20 that uses a non-parallel beam such as a fan beam or a cone beam, with a slight change in a way apparent to the person skilled in the art. The method of the present embodiment can also be applied to a setting other than that such as the number of pixels in FIG. 1B. Formulae (4) and (5) can also be expressed in other mathematically equivalent formats. For example, unlike that of the aforementioned, for the system matrix W, the arrangement of sampling points for the space corresponding to the total number of pixels is associated to the column direction, and the arrangement of the sampling points for the irradiation and detection corresponding to the interval in the detection direction and the detection element is associated to the row direction. Correspondingly, X in Formula (4) can also be expressed as a row vector according to the position of each pixel. In this case, formulae corresponding to Formulae (4) and (5) are subjected to a transpose operation on each side. This transpose operation has an expressional influence such that the rows and columns of the matrix and the vector are exchanged, and the order of the matrix operation to the vector is changed from "left to right" to "right to left". When a vector is alternatively described as a "column or row vector" and the array of elements of the corresponding matrix is similarly alternatively described as being in a "column direction or row direction", the alternative elements are combined and selected according to the same order in such alternative descriptions. Since the selection of the expressions does not affect the essence of the present application, X or the like obtained by vectorizing a sinogram as described in Formula (4) is expressed by a column vector, and the matrix of the system matrix or the like will be described on the basis of notation to operate in a left-to-right manner, unless otherwise noted.

The present inventors found that an exact solution may be obtained even in a scan angle range of less than (180°-180°/number of projections), and further found that three operating parameters, namely a number of detection elements, a number of projections meaning a number of samples in a detection direction, and a scan angle range, may be adjusted as the appropriate design in the step of irradiation to obtain an exact solution described above. The present inventors also found that in this case, when a number of detection elements and a number of projections meaning a number of samples are larger than a resolution of a tomographic image, the probability of the existence of an exact solution increases, and that the larger a number of samples is than a resolution, the more the probability of the existence of an exact solution increases and simultaneously the more the range in which an exact solution exists enlarges, expanding in a direction in which the scan angle range is smaller. As examples thereof, a case where a number of detection elements is larger than a resolution, a case where a number of projections is larger than a resolution, and a case where a number of detection elements and a number of projections are larger than a resolution are described below.

(1) Case where a Number of Detection Elements is Larger than a Resolution

An example with a resolution of 2, namely a tomographic image with 2×2 pixels, a number of detection elements being 4, a number of projections being 2, and a scan angle range being 22° is described below.

Figure 3:
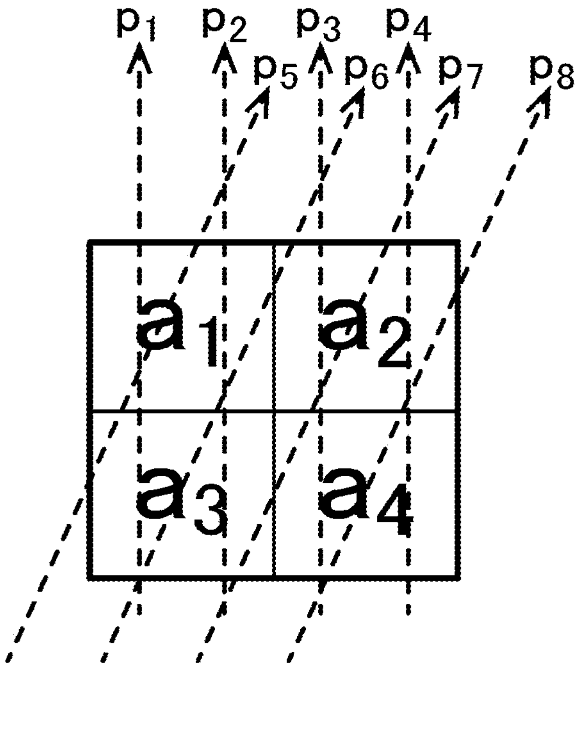
FIG. 3 is a diagram showing a relationship among pixels of an example of a tomographic image, irradiation of wave- or particle beams, and positions of detection elements, when a number of detection elements is larger 15 than a resolution.

In this case, a geometrical arrangement is as shown in FIG. 3. Thus, the values of $p_1$ to $p_8$ detected by each detection element are described as represented by Formula (6) using $a_1$ to $a_4$ carrying the degree of beam attenuation by the object 2 at the position of each pixel.

[Math 4]

$$\begin{aligned} p_1 &= a_1 + a_3 \\ p_2 &= a_1 + a_3 \\ p_3 &= a_2 + a_4 \\ p_4 &= a_2 + a_4 \\ p_5 &= a_1 + a_3 \\ p_6 &= a_1 + a_2 + a_3 \\ p_7 &= a_2 + a_3 + a_4 \\ p_8 &= a_2 + a_4 \end{aligned} \tag{6}$$

Formula (6) in a form of a matrix is expressed by FIG. 18, and the system matrix W is expressed by Formula (7).

[Math 5]

$$W = \begin{pmatrix} 1 & 0 & 1 & 0 \\ 1 & 0 & 1 & 0 \\ 0 & 1 & 0 & 1 \\ 0 & 1 & 0 & 1 \\ 1 & 0 & 1 & 0 \\ 1 & 1 & 1 & 0 \\ 0 & 1 & 1 & 1 \\ 0 & 1 & 0 & 1 \end{pmatrix} \tag{7}$$

Here, since the system matrix W is not a square matrix, $a_1$ to $a_4$ cannot be obtained by multiplying an inverse matrix from the left-hand side in FIG. 18. Then, the system matrix W is squared by decimating the elements of four row vectors from the elements of the eight row vectors constituting the system matrix W. This squared matrix is called a square system matrix $W_{SQ}$.

In this case, since the elements of four row vectors are selected by decimating the elements of four row vectors from the elements of the eight row vectors, there are ${}_8C_4=70$ combinations in total. Among them, there are nine combinations in which a square system matrix $W_{SQ}$ has an inverse matrix. One of the combinations includes the row vectors surrounded by dotted lines, and in this context, Formula (8) holds for the obtained square system matrix $W_{SQ}$.

[Math 6]

$$\begin{pmatrix} p_1 \\ p_3 \\ p_6 \\ p_7 \end{pmatrix} = \begin{pmatrix} 1 & 0 & 1 & 0 \\ 0 & 1 & 0 & 1 \\ 1 & 1 & 1 & 0 \\ 0 & 1 & 1 & 1 \end{pmatrix} \begin{pmatrix} a_1 \\ a_2 \\ a_3 \\ a_4 \end{pmatrix} \quad (8)$$

By multiplying the inverse matrix $W_{SQ}^{-1}$ from the left-hand side, $a_1$ to $a_4$ can be obtained as expressed by Formula (9), and thereby a tomographic image can be obtained.

[Math 7]

$$\begin{aligned} a_1 &= p_1 - p_7 + p_3 \\ a_2 &= p_6 - p_1 \\ a_3 &= p_7 - p_3 \\ a_4 &= p_3 - p_6 + p_1 \end{aligned} \quad (9)$$

(2) Case where a Number of Projections is Larger than a Resolution

The following is an example with a resolution of 2, namely a tomographic image with 2×2 pixels, a number of detection elements being 2, a number of projections being 6, and a scan angle range being 65.2°.

Figure 4:
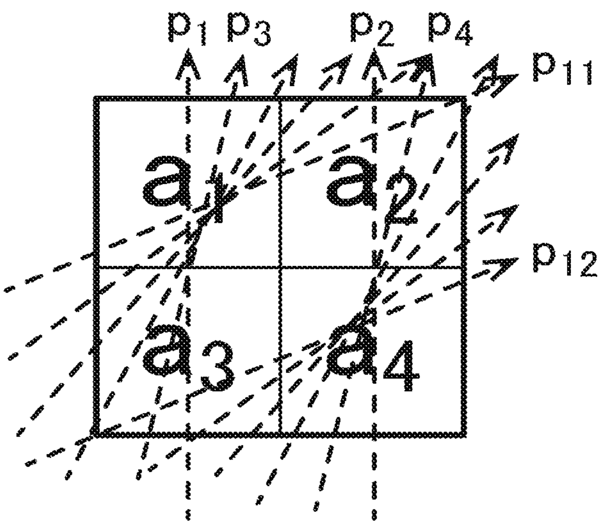
FIG. 4 is a diagram showing a relationship among pixels of an example of a tomographic image, irradiation of wave- or particle beams, and positions of detection elements, when a number of projections is larger than a resolution. 20

In this case, a geometrical arrangement is as shown in FIG. 4. Thus, the values of $p_1$ to $p_8$ detected by each detection element are described as represented by Formula (10) using $a_1$ to $a_4$ carrying the degree of beam attenuation by the object 2 at the position of each pixel.

[Math 8]

$$\begin{aligned} p_1 &= a_1 + a_3 \\ p_2 &= a_2 + a_4 \\ p_3 &= a_1 + a_3 \\ p_4 &= a_2 + a_4 \\ p_5 &= a_1 + a_3 \\ p_6 &= a_2 + a_4 \\ p_7 &= a_1 + a_2 + a_3 \\ p_8 &= a_2 + a_3 + a_4 \\ p_9 &= a_1 + a_2 + a_3 \\ p_{10} &= a_2 + a_3 + a_4 \\ p_{11} &= a_1 + a_2 \\ p_{12} &= a_3 + a_4 \end{aligned} \quad (10)$$

Formula (10) in a form of matrix is expressed by FIG. 19, and the system matrix W is expressed by Formula (11).

[Math 9]

$$W = \begin{pmatrix} 1 & 0 & 1 & 0 \\ 0 & 1 & 0 & 1 \\ 1 & 0 & 1 & 0 \\ 0 & 1 & 0 & 1 \\ 1 & 0 & 1 & 0 \\ 0 & 1 & 0 & 1 \\ 1 & 1 & 1 & 0 \\ 0 & 1 & 1 & 1 \\ 1 & 1 & 1 & 0 \\ 0 & 1 & 1 & 1 \\ 1 & 1 & 0 & 0 \\ 0 & 0 & 1 & 1 \end{pmatrix} \quad (11)$$

In this case, since the elements of four row vectors are selected by decimating the elements of eight row vectors from the elements of the 12 row vectors, there are ${}_{12}C_4$=495 combinations in total. Among them, there are 160 combinations in which a square system matrix $W_{SQ}$ has an inverse matrix. One of the combinations includes the row vectors surrounded by dotted lines, and in this context, Formula (12) holds for the obtained square system matrix $W_{SQ}$.

[Math 10]

$$\begin{pmatrix} p_1 \\ p_2 \\ p_9 \\ p_{10} \end{pmatrix} = \begin{pmatrix} 1 & 0 & 1 & 0 \\ 0 & 1 & 0 & 1 \\ 1 & 1 & 1 & 0 \\ 0 & 1 & 1 & 1 \end{pmatrix} \begin{pmatrix} a_1 \\ a_2 \\ a_3 \\ a_4 \end{pmatrix} \quad (12)$$

By multiplying the inverse matrix $W_{SQ}^{-1}$ from the left-hand side, $a_1$ to $a_4$ can be obtained as expressed by Formula (13), and thereby a tomographic image can be obtained.

[Math 11]

$$\begin{aligned} a_1 &= p_1 + p_2 - p_{10} \\ a_2 &= p_9 - p_1 \\ a_3 &= p_{10} - p_2 \\ a_4 &= p_1 + p_2 - p_9 \end{aligned} \quad (13)$$

(3) Case where a Number of Detection Elements and a Number of Projections are Larger than a Resolution The following is an example with a resolution of 2, namely a tomographic image with 2×2 pixels, a number of detection elements being 4, a number of projections being 4, and a scan angle range being 54°.

Figure 5:
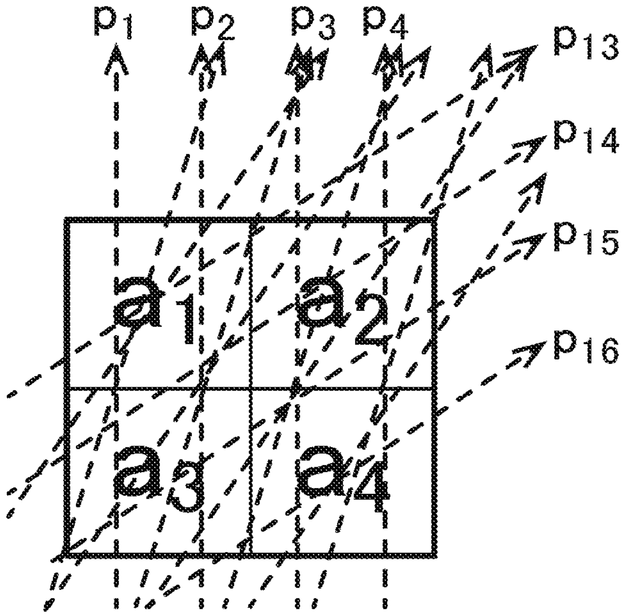
FIG. 5 is a diagram showing a relationship among pixels of an example of a tomographic image, irradiation of wave- or particle beams, and positions of detection elements, when a number of detection elements and a number of projections are larger than a resolution.

In this case, a geometrical arrangement is as shown in FIG. 5. Thus, the values of $p_1$ to $p_{16}$ detected by each detection element are described as represented by Formula (14) using $a_1$ to $a_4$ carrying the degree of beam attenuation by the object 2 at the position of each pixel.

[Math 12]

$$\begin{aligned} p_1 &= a_1 + a_3 \\ p_2 &= a_1 + a_3 \\ p_3 &= a_2 + a_4 \\ p_4 &= a_2 + a_4 \\ p_5 &= a_1 + a_3 \\ P_6 &= a_1 + a_2 + a_3 \\ p_7 &= a_2 + a_3 + a_4 \\ p_8 &= a_2 + a_4 \\ p_9 &= a_1 + a_3 \\ p_{10} &= a_1 + a_2 + a_3 \\ p_{11} &= a_2 + a_3 + a_4 \\ p_{12} &= a_2 + a_4 \\ p_{13} &= a_1 + a_2 \\ p_{14} &= a_1 + a_2 + a_3 \\ p_{15} &= a_2 + a_3 + a_4 \\ p_{16} &= a_3 + a_4 \end{aligned} \quad (14)$$

Formula (14) in a form of a matrix is expressed by FIG. 20, and the system matrix W is expressed by Formula (15).

[Math 13]

$$W = \begin{pmatrix} 1 & 0 & 1 & 0 \\ 1 & 0 & 1 & 0 \\ 0 & 1 & 0 & 1 \\ 0 & 1 & 0 & 1 \\ 1 & 0 & 1 & 0 \\ 1 & 1 & 1 & 0 \\ 0 & 1 & 1 & 1 \\ 0 & 1 & 0 & 1 \\ 1 & 0 & 1 & 0 \\ 1 & 1 & 1 & 0 \\ 0 & 1 & 1 & 1 \\ 0 & 1 & 0 & 1 \\ 1 & 1 & 0 & 0 \\ 1 & 1 & 1 & 0 \\ 0 & 1 & 1 & 1 \\ 0 & 0 & 1 & 1 \end{pmatrix}. \quad (15)$$

In this case, since the elements of four row vectors are selected by decimating the elements of 12 row vectors from the elements of the 16 row vectors, there are ${}_{16}C_4$=1820 combinations in total. Among them, there are 465 combinations in which the square system matrix $W_{SQ}$ has an inverse matrix. One of the combinations includes the row vectors surrounded by dotted lines, and in this context, Formula (16) holds for the obtained square system matrix $W_{SQ}$.

[Math 14]

$$\begin{pmatrix} p_2 \\ p_3 \\ p_{10} \\ p_{11} \end{pmatrix} = \begin{pmatrix} 1 & 0 & 1 & 0 \\ 0 & 1 & 0 & 1 \\ 1 & 1 & 1 & 0 \\ 0 & 1 & 1 & 1 \end{pmatrix} \begin{pmatrix} a_1 \\ a_2 \\ a_3 \\ a_4 \end{pmatrix} \quad (16)$$

By multiplying the inverse matrix $W_{SQ}^{-1}$ from the left-hand side, $a_1$ to $a_4$ can be obtained as represented by Formula (17), and thereby a tomographic image can be obtained.

[Math 15]

$$\begin{aligned} a_1 &= p_2 + p_1 - p_{11} \\ a_2 &= p_{10} - p_2 \\ a_3 &= p_{11} - p_3 \\ a_4 &= p_2 + p_3 - p_{10} \end{aligned} \quad (17)$$

Figure 6A:
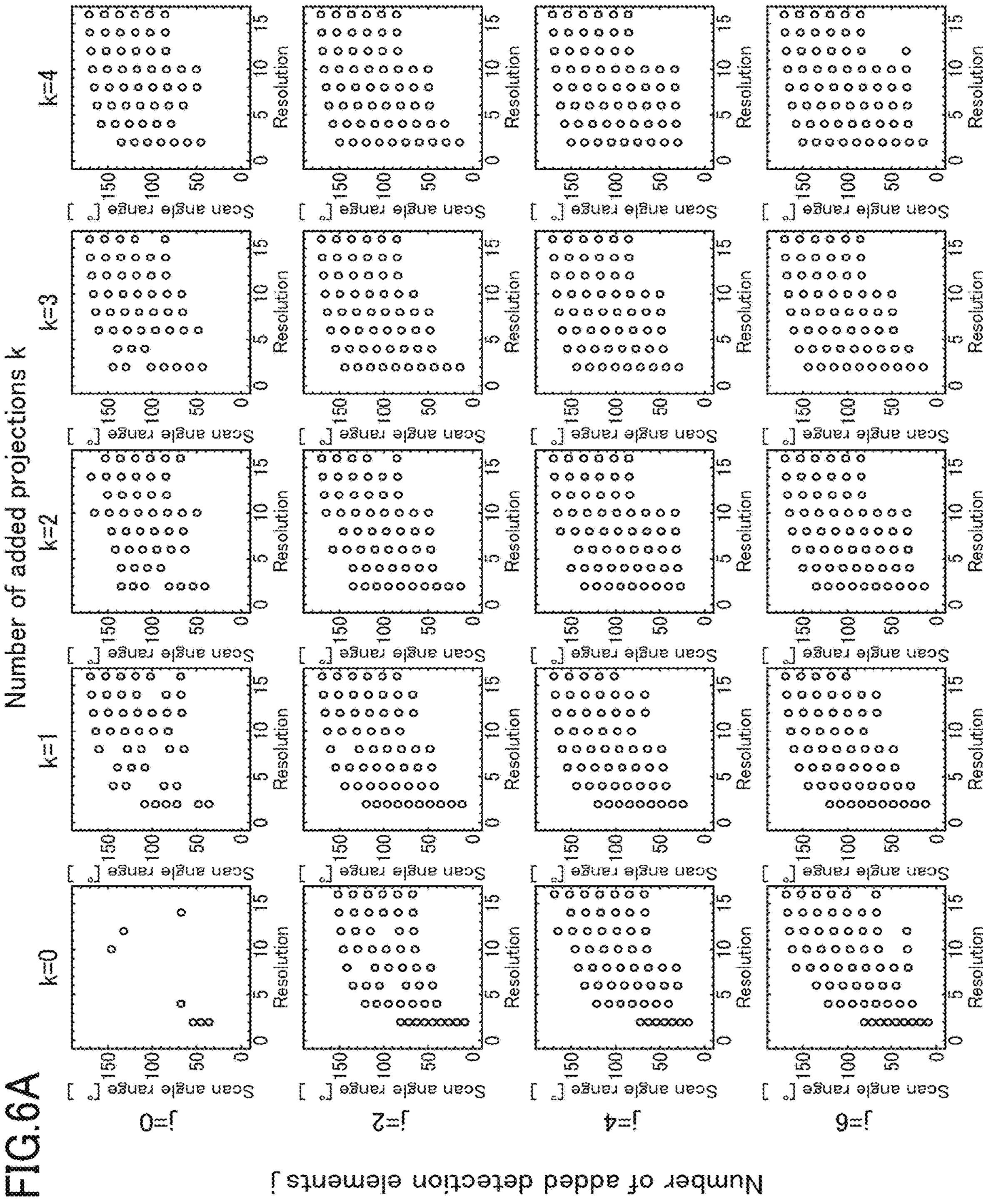
FIG. 6A is a diagram showing resolutions and scan angle ranges for which exact solutions exist with respect to the numbers of added detection elements and projections in relation to resolutions up to 16.
Figure 6B:
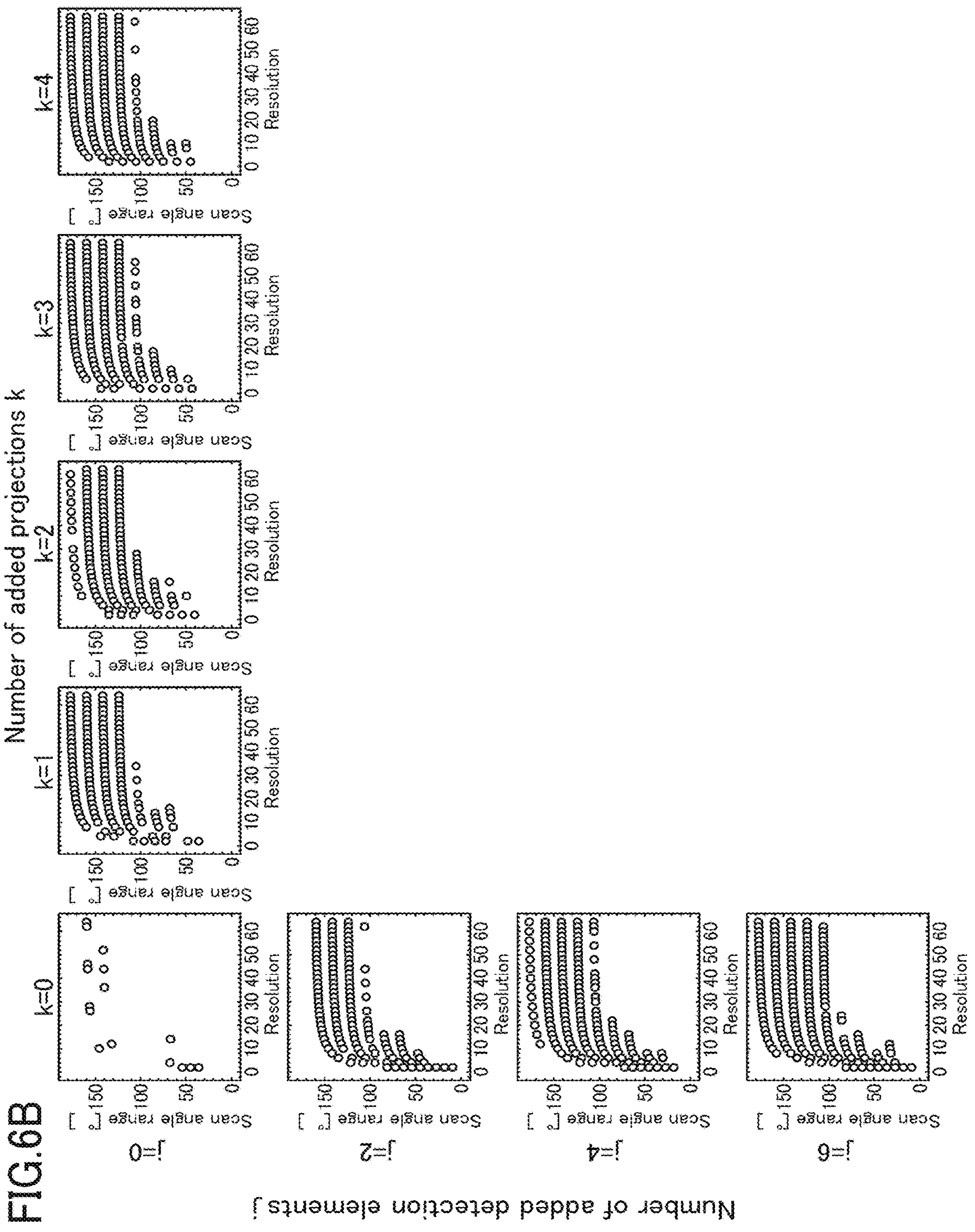
FIG. 6B is a diagram showing resolutions and scan angle ranges for which exact solutions exist with respect to the numbers of added detection elements and projections in relation to resolutions up to 64.

The above describes the cases where a number of detection elements and/or a number of projections is larger than a resolution. As described above, however, the present inventors found that there may be an exact solution for a scan angle range of less than (180°-180°/number of projections) even if a number of detection elements and a number of projections are the same as a resolution. Then, the present inventors studied resolutions and scan angle ranges for which exact solutions exist with respect to the numbers of added detection elements and projections in relation to resolutions by numerical computation. The results are summarized in FIGS. 6A and 6B. FIG. 6A shows resolutions and scan angle ranges for which exact solutions exist with respect to the numbers of added detection elements and projections in relation to resolutions up to 16. FIG. 6B shows resolutions and scan angle ranges for which exact solutions exist with respect to the numbers of added detection elements and projections in relation to resolutions up to 64. In FIG. 6B, figures showing a case where both detection elements and projections are added are omitted. The results shown in FIGS. 6A and 6B were obtained under the same computational experiment conditions as those employed in the section (Verification by Computer Simulation (Example)) described later, with variations of an additional number of detection elements, an additional number of projections, a scan angle range, and a resolution. As is obvious from FIGS. 6A and 6B, an exact solution can be obtained by appropriately selecting a number of detection elements, a number of projections, and a scan angle range in a scan angle range of less than (180°-180°/number of projections). It can also be understood that when a number of detection elements and a number of projections meaning a number of samples are larger than a resolution of a tomographic image, the probability of the existence of an exact solution increases, and that the larger a number of samples is than a resolution, the more the probability of the existence of an exact solution increases and simultaneously the more a range in which an exact solution exists enlarges, expanding in a direction in which the scan angle range is smaller. Accordingly, by appropriately selecting a number of detection elements and a number of projections, for example, an exact solution can be obtained in a desired scan angle range of less than (180°-180°/number of projections). For instance, the example disclosed in the above Non-Patent Document 6 requires a scan angle range of 160° or less. However, if appropriate numbers of detection elements and projections for which an exact solution can be obtained in a scan angle range of 160° or less are sought, a reconstructed image on the basis of an exact solution can be obtained by performing measurement with the thus-found numbers of detection elements and projections.

Here, when a detection element is added, there may be three cases where (1) a detection element is added by reducing a size of the detection element (typically, a detection element is added by reducing a size of the detection element to maintain the area of a group of detection elements); (2) a detection element is added without changing its size; and (3) a detection element is added by reducing a size of the detection element. In all cases (1) to (3), in view of the mathematical process described later, detection elements, added in the same number, will have the same effect in terms of obtaining an exact solution by obtaining a square system matrix having an inverse matrix. Accordingly, the results shown in FIGS. 6A and 6B obtained by evaluation focusing on the structure of a system matrix alone and not based on information of a physical length such as the relative size of a group of detection elements and an object to be measured, are sufficient to determine conditions for obtaining an exact solution.

In addition, a reconstructed image obtained by the present embodiment has a high quality based on an exact solution, which is useful as learning data for a machine learning system to estimate a reconstructed image from an input tomographic image.

The above is explained in a generalized way as described below.

<Process for Generating an Inverse Discrete Radon Transform Matrix>

When a two-dimensional image with N×N pixels (N is a positive integer) is reconstructed by tomographic imaging, the number of detection elements 22 of the detection device 20 is N in a conventional method, but such a number is (N+j) (j is an integer of 0 or more) in the present embodiment. In a conventional method, sampling in a detection direction θ is performed in a range of 0 to 180°, namely in N directions without overlapping in a scan angle range of 180° at an interval of (180/N)° as described above. In contrast, the sampling in a detection direction according to the present embodiment is performed in N+k directions (k is an integer of 0 or more) without overlapping in a scan angle range φ of less than (180°-180°/number of projections), for example at an interval of (φ/(N+k−1))°. Intervals of the sampling (i.e., intervals in a detection direction) may be different from each other, and need not be equal intervals such as φ/(N+k−1)°. In such a way, the sampling in a detection direction is performed with (N+j) detection elements instead of N detection elements, and in N+k directions instead of N directions.

On the basis of the number of detection elements (N+j), the number of projections (N+k), and the scan angle range φ, a system matrix is determined. The system matrix herein determined only has (N+k)×(N+j) elements in a column direction corresponding to the detection direction and each of the detection elements, and N×N elements in a row direction corresponding to the number of pixels of a tomographic image. In order to allow the computation of an inverse matrix, the elements of (j+k)×N+j×k row vectors having N×N elements located in appropriate positions are removed from the system matrix W to generate a square system matrix $W_{SQ}$. If the elements of the row vectors removed are appropriate, the square system matrix $W_{SQ}$ has an inverse matrix. From the square system matrix $W_{SQ}$, an inverse discrete Radon transform matrix that is the inverse matrix $W_{SQ}^{-1}$ thereof is computed. Here, any appropriate well-known methods such as the cofactor method and the sweep-out method may be used in the computation of the inverse matrix $W_{SQ}^{-1}$.

<Process for Generating Reconstructed Image>

Meanwhile, the object 2 is disposed between the emission device 10 and the detection device 20 having detection elements 22 to obtain a tomographic image of the object 2. Detection is performed in N+k directions without overlapping under the irradiation of the beam 4 from the emission device 10. Typically, this beam 4 irradiates continuously, and the orientation of the object 2, the emission device 10, and the detection device 20 (direction of detection) moves smoothly while the signals from the detection elements 22 of the detection device 20 are electrically sampled. A typical example of the irradiation and detection in the non-overlapping N+k directions is sampling with a timing at an interval of (φ/N+k−1))°. The obtained signals are organized into data that can be used to generate a sinogram, if necessary, by performing processing such as corrections and scale conversions for the physical characteristics of the instruments, and by arranging the sequence order. The process of obtaining the sinogram is the irradiation and detection process, which is a discrete Radon transform. From this sinogram, a column vector can be obtained by rearranging the elements in such an order so as to match the sequence of the column direction of the system matrix W. This vector is referred to as the first vector in the present embodiment. Since the first vector X' has a value of a sinogram, it has (N+k)×(N+j) elements.

A vector decimation process for decimating the elements of the first vector X' corresponding to the elements of a row vector that was removed during the generation of the square system matrix $W_{SQ}$, will yield a second vector $X_{SQ}'$, which is a column vector with N×N elements that can satisfy the relationship represented by Formula (4) with the square system matrix $W_{SQ}$. Since the second vector $X_{SQ}'$ satisfies the relationship represented by Formula (4) with the square system matrix $W_{SQ}$, the relationship of Formula (5) holds using the inverse discrete Radon transform matrix $W_{SQ}^{-1}$ which is the inverse matrix of the square system matrix $W_{SQ}$, and the inverse discrete Radon transform process gives a third vector $X_{SQ}$ for the reconstructed image. The reconstructed image is obtained by de-vectorizing the sequence of the third vector $X_{SQ}$ back into an image with N×N pixels, by means of an inverse operation of vectorization. The tomographic image for one slice is thereby reconstructed.

The process of the present embodiment is divided into two sections, namely the inverse discrete Radon transform matrix generation process and the reconstructed image generation process described above. A user who normally captures a reconstructed image performs the above reconstructed image generation process from irradiation and detection to the generation of a reconstructed image. In other words, the user does not necessarily have to perform an inverse discrete Radon transform matrix generation process from the system matrix generation corresponding to the above operating parameters to the inverse discrete Radon transform matrix generation. The inverse discrete Radon transform matrix generation process is required for a situation in which a tomographic imaging system is manufactured, installed, and maintained; namely, this process is performed by the equipment manufacturer or the like. If elements of a row vector to be decimated and an inverse discrete Radon transform matrix $W_{SQ}^{-1}$ are to be obtained, the users who intend to image a reconstructed image need only use them for their own measurements.

It should be noted that the reconstructed image generation process is the transposition of the order of matrices and vectors and the operation of the matrix multiplication and does not include within its scope the processing that is problematic in terms of computational processing volume, such as an iterative approximation. In the present embodiment, a reconstructed image generation process, which is used in the user's ordinary imaging, can be performed with a sufficiently light computational burden merely by using the elements of row vectors to be decimated and the inverse discrete Radon transform matrix $W_{SQ}^{-1}$ prepared by the inverse discrete Radon transform matrix generation process. This brings a high degree of practicality to the present embodiment. This is because the computational burden of the most frequent processes of acquiring a tomographic image is very small. In particular, the method of the present embodiment is extremely advantageous for applications in which many slices are repeatedly imaged to obtain a three-dimensional volume image. In addition to the fact that the repetition requires no inverse discrete Radon transform matrix generation process, the reconstructed image generation process is suitable for computation processing using many-core processors such as GPGPU (general-purpose computing on graphics processing units), and therefore, the processing speed can be expected to increase in the future.

In addition, the system matrix W, the square system matrix $W_{SQ}$, and the inverse matrix $W_{SQ}^{-1}$ of the system matrix $W_{SQ}$, all of which reflect the geometric aspect, are included only in the inverse discrete Radon transform matrix generation process, and these are separated from the reconstructed image generation process for measurement. This essentially separates the problem of convergence when using iteration in algebraic approaches from the noise aspect for measurement. As a result, the present embodiment also has an advantage that the phenomenon caused by approximate solutions that are unrelated to noise is less likely to occur, and various noise reduction processes commonly employed in image processing are more likely to be effective as intended.

<Specific Approach for Determining Elements of Row Vectors to be Decimated>

As discussed above, whether the inverse discrete Radon transform matrix $W_{SQ}^{-1}$ is obtained as the inverse matrix of the square system matrix $W_{SQ}$ depends on the appropriateness of elements of row vectors to be decimated. The approach is not particularly limited as long as it can generate a square system matrix having an invert matrix as a result. Here, a randomized algorithm utilizing a decision by a rank is described below.

The total number of rows in the system matrix W is (N+k)×(N+j). Of these, the number of rows left to make the matrix into a square matrix is N×N, and the total number of row vectors to be decimated is (j+k)×N+j×k. From the range [1, (N+k)×(N+j)] of integers in the index (row number) that identifies the rows, the sequences of either N×N to keep or (j+k)×N+j×k to decimate are determined. For this determination, a randomized selection approach is adopted. That is to say, either the N×N units to keep or the (j+k)×N+j×k units to decimate is randomly determined by numerically generated random numbers, and thereby the decimation sequence {m} can be finally determined. Once the decimation sequence {m} is determined, the square system matrix $W_{SQ}$ can be obtained from the system matrix W by a corresponding decimation process. Next, the rank is calculated for the obtained square system matrix $W_{SQ}$. The calculated rank is the same value as N×N if the square system matrix $W_{SQ}$ has an inverse matrix, and if it does not have an inverse matrix, the calculated rank is smaller than N×N. Therefore, the rank value serves as a reference to determine whether the square system matrix $W_{SQ}$ can have an inverse matrix or not. If the rank does not match N×N, whether the square system matrix $W_{SQ}$ has an inverse matrix may be determined by selecting the decimation sequence {m} using a randomized algorithm based on other random numbers again and by calculating the rank. If such randomized algorithm is adopted, the matrix decimation process can be executed at a practical speed.

Here, if the same combination of row vectors is selected by different decimation of row vectors, the same square system matrix $W_{SQ}$ will be obtained. The present inventors focused on this point and conceived of an efficient method for selecting row vectors as described below.

The decimation in the above "(3) Case where a number of detection elements and a number of projections are larger than a resolution" is hereinafter described as an example.

Figures 7, 8:
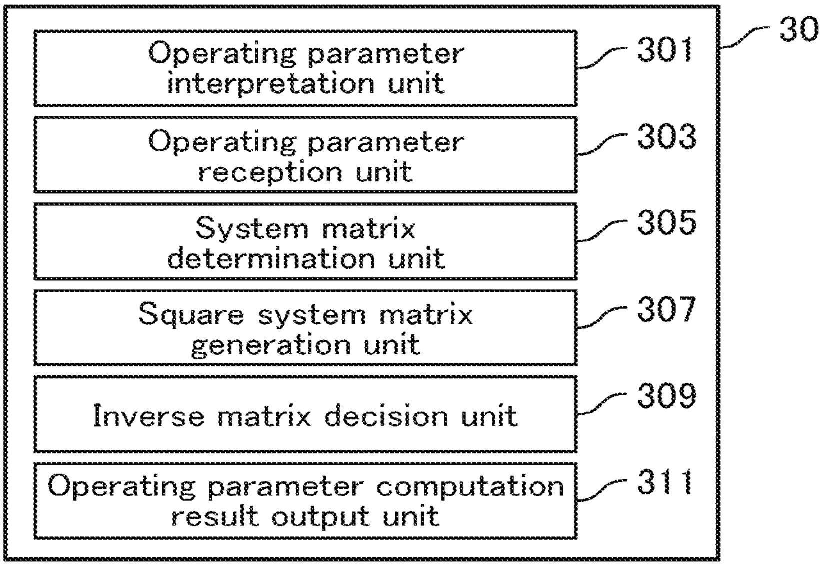
FIG. 7 is a diagram showing an example of an efficient method for selecting a row vector in a matrix decimation process according to an embodiment of the present invention.
FIG. 8 is a block diagram showing a functional configuration of an operating parameter computing device according to an embodiment of the present invention.

Referring to FIG. 7, the row vector corresponding to $p_1$ is (1010), and the row vectors corresponding to $p_2$, $p_5$, and $p_9$ are the same row vectors (1010). Thus, the row vectors corresponding to $p_2$, $p_5$, and $p_9$ are decimated.

Next, the row vector corresponding to $p_3$ is (0101), and the row vectors corresponding to $p_8$ and $p_{12}$ are the same row vectors (0101). Thus, the row vectors corresponding to $p_8$ and $p_{12}$ are decimated.

Subsequently, the row vector corresponding to $p_6$ is (1110), and the row vectors corresponding to $p_{10}$ and $p_{14}$ are the same row vectors (1110). Thus, the row vectors corresponding to $p_{10}$ and $p_{14}$ are decimated.

Further, the row vector corresponding to $p_7$ is (0111), and the row vectors corresponding to $p_{11}$ and $p_{15}$ are the same row vectors (0111). Thus, the row vectors corresponding to $p_{11}$ and $p_{15}$ are decimated.

By the above decimation process, remaining row vectors are different from each other. Since six row vectors remain, the number of combinations for generating the square system matrix $W_{SQ}$ can be reduced from ${}_{16}C_4=1820$ to ${}_{6}C_4=15$. By first decimating (removing) overlapping row vectors in such a way, the number of row vectors that are candidates for selection can be reduced, leading to the reduction of the number of combinations. As a result, computational volume required for determining whether an inverse matrix is included can be reduced.

<Method for Improving Image Quality Utilizing Decimated Overlapping Row Vectors>

The present inventors also focused on the fact that the same square system matrix $W_{SQ}$ will be obtained when the same combination of row vectors is selected by a different decimation of row vectors, and conceived of an efficient method for improving the quality of a reconstructed image as described below.

For example, a square system matrix $W_{SQ}$ made up of the elements of the row vectors corresponding to $p_2$, $p_5$, $p_{10}$, and $p_{11}$ has an inverse matrix as described above. However, since the elements of a row vector corresponding to $p_1$ are the same as the elements of the row vector corresponding to $p_2$ as described above, the square system matrix $W_{SQ}$ made up of the elements of $p_1$, $p_3$, $p_{10}$, and $p_{11}$ is the same as the square system matrix $W_{SQ}$ made up of the elements of the row vectors corresponding to $p_2$, $p_5$, $p_{10}$, and $p_{11}$ and has an inverse matrix. In contrast, since $p_1$ and $p_2$ are independently measured by different detection elements, the SN ratio of a reconstructed image is improved by superimposing a reconstructed image obtained by $p_2$, $p_3$, $p_{10}$, and $p_{11}$ and a reconstructed image obtained by $p_1$, $p_3$, $p_{10}$, and $p_{11}$, and improved image quality can be achieved. This is because the higher the number of measurement is, the higher the measurement accuracy is obtained in general, and the SN ratio is said to be $n^{1/2}$ times when measurement is carried out n times. Similarly, since the elements of the row vectors corresponding to $p_5$ and $p_9$ are the same as the elements of the row vector corresponding to $p_2$ as described above, the SN ratio of a reconstructed image is further improved by superimposing reconstructed images obtained by $p_2$, $p_3$, $p_{10}$, and $p_{11}$; $p_1$, $p_3$, $p_{10}$, and $p_{11}$; $p_5$, $p_3$, $p_{10}$, and $p_{11}$; and $p_9$, $p_3$, $p_{10}$, and $p_{11}$, and improved image quality can be achieved.

As in the foregoing, a reconstructed image with high accuracy can be efficiently obtained with the least amount of computational volume by the approach obtained by combining (1) a decimation method for quickly finding a combination having an inverse matrix, and (2) an approach for increasing accuracy using a reconstructed image on the basis of a combination of inverse matrices including elements of row vectors decimated by the above decimation method.

Specific Embodiments of the Present Invention

Specific embodiments of the present invention are described below by referring to figures and drawings. Descriptions overlapping with those in the aforementioned (Principle) are omitted.

FIG. 1B is a diagram showing the entire configuration of a tomographic imaging system according to the present embodiment. The tomographic imaging system 1 includes an emission device 10, a detection device 20, an operating parameter computing device 30, an inverse discrete Radon transform matrix generation device 40, and a reconstructed image generation device 50. The emission device 10, the detection device 20, the operating parameter computing device 30, the inverse discrete Radon transform matrix generation device 40, and the reconstructed image generation device 50 need not be configured as a single physical device, and a part or the entirety thereof may be configured each as an individually separate physical device. In this context, the devices configured as individually separate physical devices may be connected to each other through a wired/wireless computer network. Each of the emission device 10, detection device 20, operating parameter computing device 30, inverse discrete Radon transform matrix generation device 40, and reconstructed image generation device 50 need not be configured as a single physical device and may be made up of multiple physical devices.

FIG. 8 is a block diagram showing a functional configuration of an operating parameter computing device according to the present embodiment.

The operating parameter computing device 30 includes an operating parameter interpretation unit 301, an operating parameter reception unit 303, a system matrix determination unit 305, a square system matrix generation unit 307, an inverse matrix decision unit 309, and an operating parameter computation result output unit 311.

If a data input by a user is a value of an operating parameter, the operating parameter interpretation unit 301 designates the value, and if an input data is a combination of the values and/or a range of the values of operating parameters, the operating parameter interpretation unit 301 designates one of the values.

The operating parameter reception unit 303 receives the values of one or two operating parameters designated from among a number of detection elements, a number of projections, and a scan angle range of less than (180°-180°/number of projections).

The system matrix determination unit 305 determines a system matrix on the basis of the values of the designated one or two operating parameters, and for an operating parameter other than the operating parameters corresponding to the values of the designated one or two operating parameters, on the basis of a predetermined value.

The square system matrix generation unit 307 generates a square system matrix by removing, from the determined system matrix, the elements of predetermined (j+k)×N+j×k row- or column vectors in total, except for the case where j=k=0.

The inverse matrix decision unit 309 decides whether an inverse matrix exists for the determined square system matrix.

The operating parameter computation result output unit 311 outputs the predetermined value of an operating parameter other than the operating parameters corresponding to the values of the designated one or two operating parameters by means of display or sound output.

Figure 9:
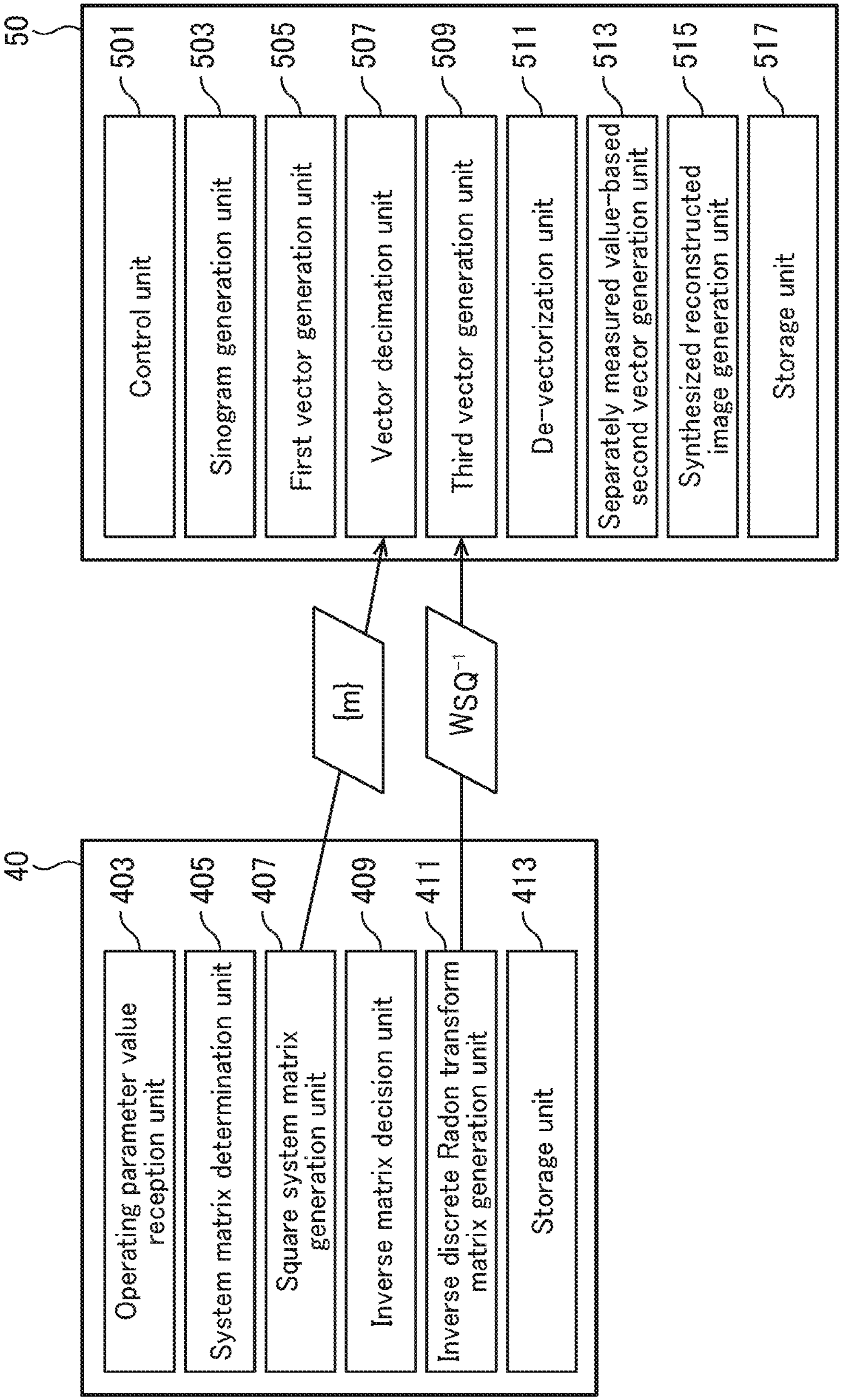
FIG. 9 is a block diagram showing a functional configuration of an inverse discrete Radon transform matrix generation device and a reconstructed image generation device according to an embodiment of the present invention.

FIG. 9 is a block diagram showing a functional configuration of an inverse discrete Radon transform matrix generation device and a reconstructed image generation device according to the present embodiment.

The inverse discrete Radon transform matrix generation device 40 includes an operating parameter reception unit 403, a system matrix determination unit 405, a square system matrix generation unit 407, an inverse matrix decision unit 409, an inverse discrete Radon transform matrix generation unit 411, and a storage unit 413.

The operating parameter reception unit 403 receives the values of the designated three operating parameters.

The system matrix determination unit 405 determines a system matrix on the basis of the values of the designated three operating parameters.

The square system matrix generation unit 407 generates a square system matrix by removing, from the determined system matrix, the elements of predetermined (j+k)×N+j×k row- or column vectors in total, except for the case where j=k=0.

The inverse matrix decision unit 409 decides whether an inverse matrix exists for the determined square system matrix.

The inverse discrete Radon transform matrix generation unit 411 generates an inverse discrete Radon transform matrix $W_{SQ}^{-1}$ that is the inverse matrix of a square system matrix $W_{SQ}$.

If it is decided that the elements of row vectors constituting the square system matrix $W_{SQ}$ include elements that are the same as those of row vectors removed in the step S207, the storage unit 413 stores indexes (row numbers) specifying the rows that correspond to the elements of the row vectors constituting the square system matrix $W_{SQ}$ and the rows that correspond to the elements of the row vectors that are the same as the row vectors removed.

The reconstructed image generation device 50 includes a control unit 501, a sinogram generation unit 503, a first vector generation unit 505, a vector decimation unit 507, a third vector generation unit 509, a de-vectorization unit 511, a separately measured value-based second vector generation unit 513, a synthesized reconstructed image generation unit 515, and a storage unit 517.

The control unit 501 controls the emission device 10 and the detection device 20 to perform detection in N+j directions without overlapping by the detection device 20 under the irradiation of the beam 4 from the emission device 10 onto the object 2.

The sinogram generation unit 503 generates a sinogram by using the signals obtained from each of the detection elements 22 of the detection device 20, and as necessary, by performing processing such as corrections and scale conversions for the physical characteristics of the instruments, and by arranging the sequence order.

The first vector generation unit 505 generates from the generated sinogram a first vector X' that is a column vector in which elements are rearranged in such an order so as to match the sequence of the column direction of the system matrix W.

The vector decimation unit 507 generates a second vector $X_{SQ}'$ by decimating the elements of the first vector X' that correspond to the elements of the row vectors removed during the generation of the square system matrix $W_{SQ}$.

The third vector generation unit 509 generates a third vector $X_{SQ}$ that gives a reconstructed image by an inverse discrete Radon transform process on the basis of Formula (5), using the inverse discrete Radon transform matrix Wso 1 generated by the inverse discrete Radon transform matrix generation unit 411 and the second vector $X_{SQ}'$.

The de-vectorization unit 511 generates a reconstructed image by a de-vectorization process in which the sequence of the third vector $X_{SQ}$ is returned to an image with N×N pixels by an inverse operation of vectorization.

On the basis of the indexes (row numbers) stored in the storage unit 413 by the square system matrix generation unit 407, the separately measured value-based second vector generation unit 513 generates a separately measured value-based second vector by replacing a part or the entirety of the elements of second vectors $X_{SQ}'$ that correspond to the indexes (row numbers) of the row vectors constituting a square system matrix $W_{SQ}$ if the square system matrix generation unit 407 decides that the elements of row vectors constituting the square system matrix $W_{SQ}$ include elements that are the same as those of row vectors removed by the square system matrix generation unit 407, with the elements of the second vectors $X_{SQ}'$ that correspond to the elements of the row vectors that are the same as the row vectors removed.

The synthesized reconstructed image generation unit 515 generates a synthesized reconstructed image with improved image quality by superimposing multiple reconstructed images generated.

The storage unit 517 stores reconstructed images generated in the step S319.

Figure 10:
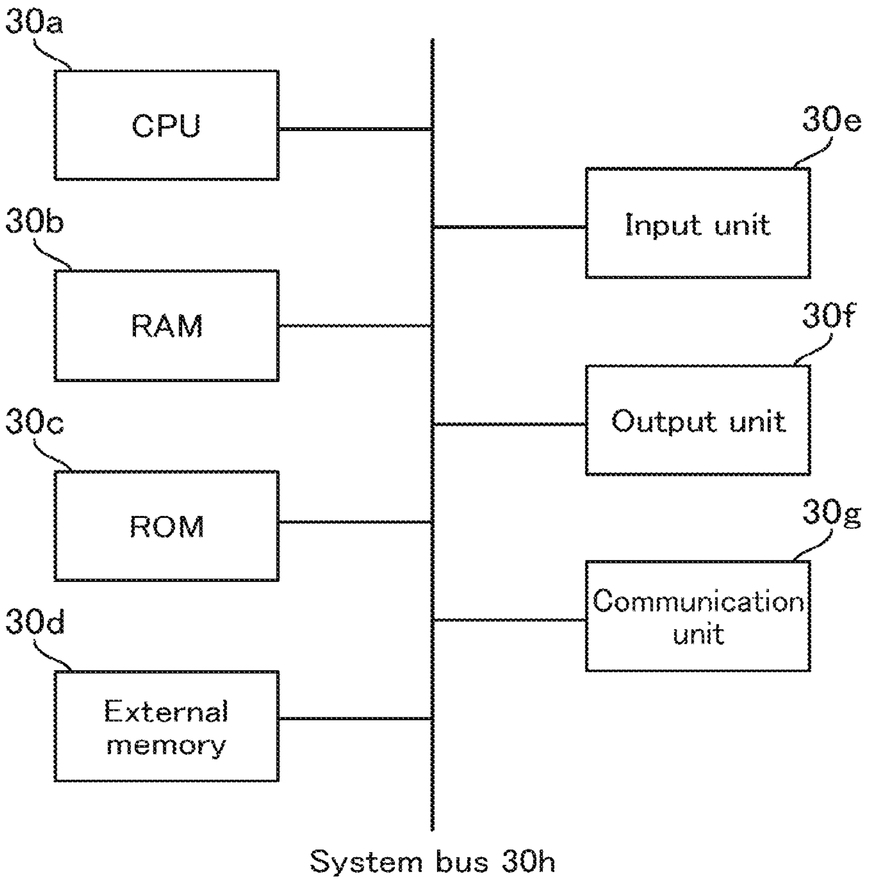
FIG. 10 is a diagram showing a hardware configuration of an operating parameter computing device 30 according to an embodiment of the present invention.

FIG. 10 is a diagram showing a hardware configuration of an operating parameter computing device 30 according to the present embodiment. The operating parameter computing device 30 includes a CPU 30*a*, a RAM 30*b*, a ROM 30*c*, an external memory 30*d*, an input unit 30*e*, an output unit 30*f*, and a communication unit 30*g*. The RAM 30*b*, ROM 30*c*, external memory 30*d*, input unit 30*e*, output unit 30*f*, and communication unit 30*g* are connected to the CPU 30*a* via a system bus 30*h*.

The CPU 30*a* comprehensively controls each device connected to the system bus 30*h*.

The ROM 30*c* and external memory 30*d* store programs for controlling the CPU 30*a* such as BIOS and OS, and various programs and data required for realizing the functions executed by a computer.

RAM 30*b* serves as a main memory or a work area of the CPU. When executing a process, the CPU 30*a* implements operations by loading necessary programs from the ROM 30*c* or the external memory 30*d* to the RAM 30*b* and executing the loaded programs.

The external memory 30*d* is constituted of a flash memory, a hard disk, a DVD-RAM and a USB memory, for example.

The input unit 30*e* receives for example an operation instruction from a user. The input unit 30*e* is constituted of input devices such as an input button, a keyboard, a pointing device, a wireless remote controller, and a microphone.

The output unit 30*f* outputs data processed by the CPU 30*a* and data stored by the RAM 30*b*, ROM 30*c*, and external memory 30*d*. The output unit 30*f* is constituted of output devices such as a CRT display, an LCD, an organic EL panel, a printer, and a speaker.

The communication unit 30*g* is an interface for direct or networked connection/communication with external devices. The communication unit 30*g* is constituted of interfaces such as a serial interface and a LAN interface.

The same also applies to the hardware configurations of the inverse discrete Radon transform matrix generation device 40 and the reconstructed image generation device 50.

Each unit of the operating parameter computing device 30 shown in FIG. 8 is implemented by programs stored in the ROM or the external memory using resources such as the CPU, RAM, ROM, external memory, input unit, output unit, and communication unit.

On the assumption of the above system configuration, an example of a tomographic imaging process of a tomographic imaging system according to the present embodiment is described below with reference to FIGS. 1 to 17E.

Descriptions overlapping with those in the aforementioned (Principle) are omitted.

<Operating Parameter Computing Process>

Figure 11A:
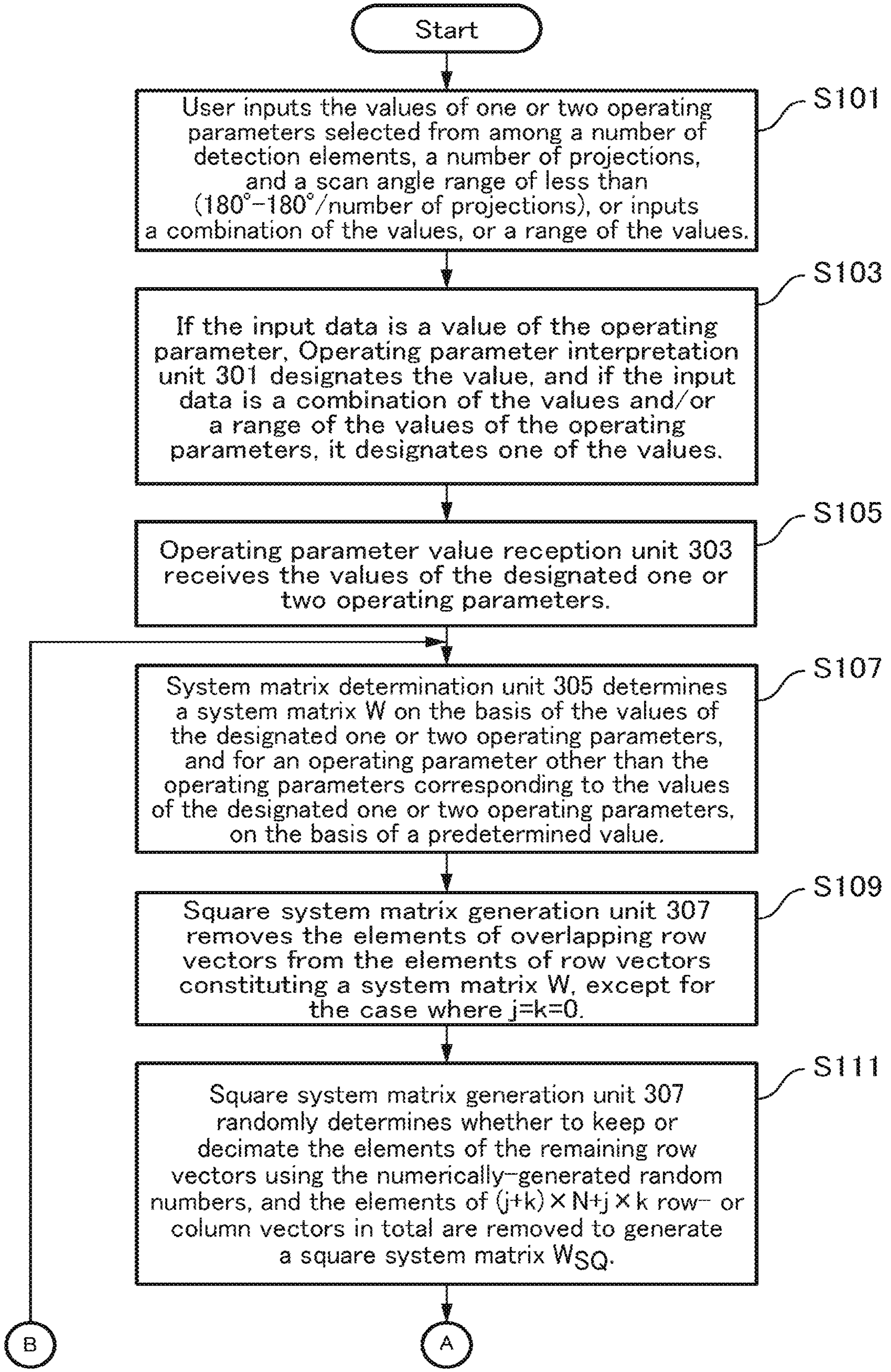
FIG. 11A is a flowchart of an example of an operating parameter computing process according to an embodiment of the present invention.
Figure 11B:
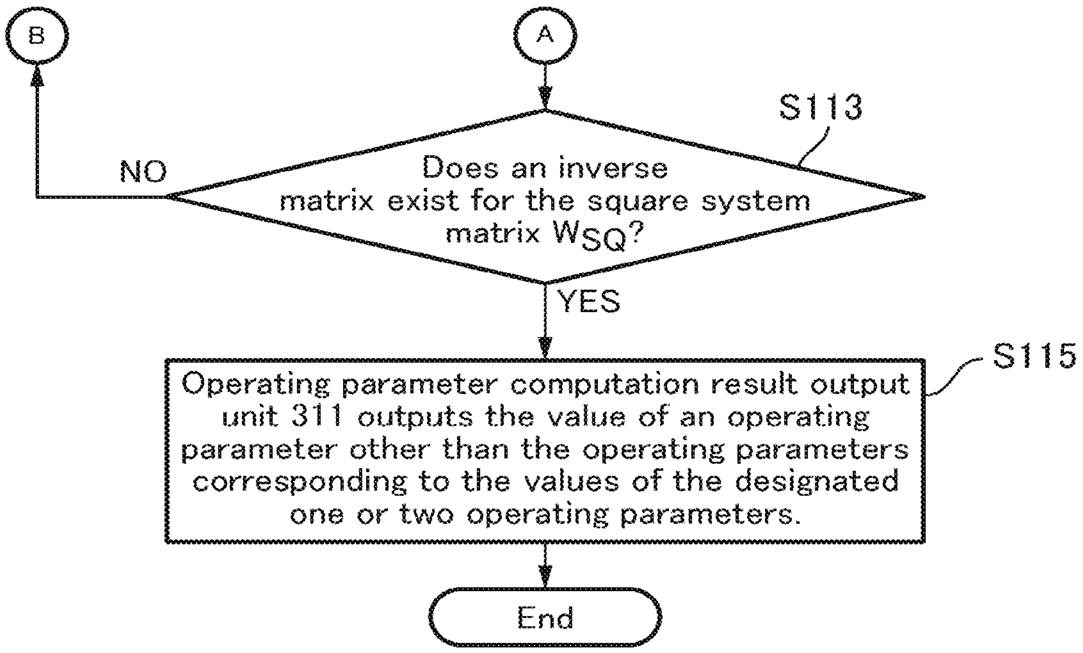
FIG. 11B is a flowchart of an example of an operating parameter computing process according to an embodiment of the present invention.

FIGS. 11A and 11B show a flowchart of an example of an operating parameter computing process according to the present embodiment.

A user inputs the values of one or two operating parameters selected from among a number of detection elements, a number of projections, and a scan angle range of less than (180°-180°/number of projections), or inputs a combination of the values, or a range of the values via the input unit 30*e* of the operating parameter computing device 30 (S101). If the input data is a value of the operating parameter, the operating parameter interpretation unit 301 of the operating parameter computing device 30 designates the value. If the input data is a combination of the values and/or a range of the values of the operating parameters, the operating parameter interpretation unit 301 designates one of the values (S103). If the input data is a combination of the values and/or a range of the values of the operating parameters, the process described below is repeated until the input combination and/or range of the values of the operating parameters exists no more. For simplicity, however, a case where the input data is a value of the operating parameter is explained below. The operating parameter value reception unit 303 of the operating parameter computing device 30 receives the values of the designated one or two operating parameters (S105).

The system matrix determination unit 305 determines a system matrix W on the basis of the values of the designated one or two operating parameters, and for an operating parameter other than the operating parameters corresponding to the values of the designated one or two operating parameters, on the basis of a predetermined value (initial value) (S107). When designated or predetermined numbers of detection elements and projections are (N+j) and (N+k) respectively (with the proviso that j and k are integers of 0 or more), the system matrix W is a matrix having (N+k)×(N+j) column- or row vectors with N×N elements, each of elements having a weight value indicative of contribution of each pixel in the two-dimensional tomographic image having N×N pigments with respect to a path of a portion of the waves or particles, the portion going toward each of the (N+j) detection elements 22, and the column- or row vectors being arranged in a row or a column direction according to each of the (N+k) detection directions while being associated with the pixels of the two-dimensional tomographic image.

The square system matrix generation unit 307 generates a square system matrix $W_{SQ}$ by removing, from the determined system matrix W, the elements of predetermined (j+k)×N+j×k row vectors in total, except for the case where j=k=0.

For the above, the elements of overlapping row vectors are first removed from the elements of row vectors constituting the determined system matrix W (S109).

Next, whether to keep or decimate the elements of the remaining row vectors is randomly determined using the numerically-generated random numbers, and the elements of (j+k)×N+j×k row- or column vectors in total are removed to generate a square system matrix $W_{SQ}$ (S111). Specifically, for the indexes (row numbers) specifying the rows of the elements of the remaining row vectors, for example, whether the index corresponds to the elements of a row vector to be kept or the elements of a row vector to be decimated is randomly determined using the numerically-generated random numbers, and thereby a decimation sequence {m} is determined. Then, the elements of a row vector corresponding to the determined decimation sequence {m} are removed to generate a square system matrix $W_{SQ}$.

The inverse matrix decision unit 309 decides whether the generated square system matrix $W_{SQ}$ has an inverse matrix (S113). Specifically, for example, the inverse matrix decision unit 309 computes the rank of the square system matrix $W_{SQ}$ and decides the existence of an inverse matrix by deciding whether the computed rank matches N×N.

If the existence of an inverse matrix is decided, the operating parameter computation result output unit 311 outputs the predetermined value of an operating parameter other than the operating parameters corresponding to the values of the designated one or two operating parameters by means of display or sound output (S115).

If the existence of no inverse matrix is decided, the process returns to the step S107 and performs the steps following the step S107 for a different predetermined value of an operating parameter other than the operating parameters corresponding to the values of the designated one or two operating parameters.

The inverse matrix decision unit 309 may return to S107, as necessary, and repeat the steps following the step S107 for a different predetermined value of an operating parameter other than the operating parameters corresponding to the values of the designated one or two operating parameters. For example, even if the step S113 has decided the existence of an inverse matrix, a range of an operating parameter other than the operating parameters corresponding to the values of the designated one or two operating parameters, for which an inverse matrix exists, can be obtained by the above repetition.

<Process for Generating Inverse Discrete Radon Transform Matrix>

Figure 12A:
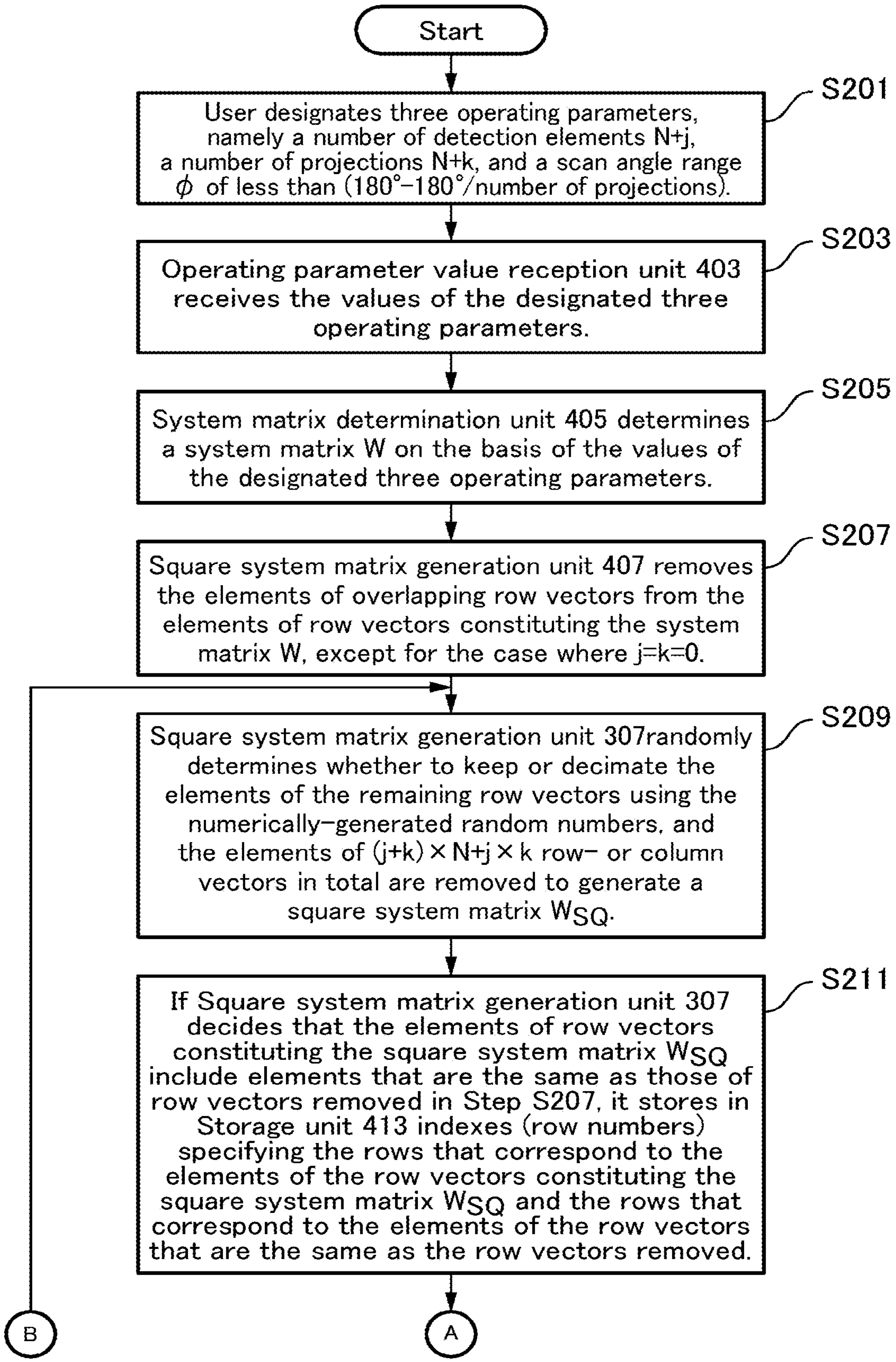
FIG. 12A is a flowchart of an example of an inverse discrete Radon transform matrix generation process according to an embodiment of the present invention.
Figure 12B:
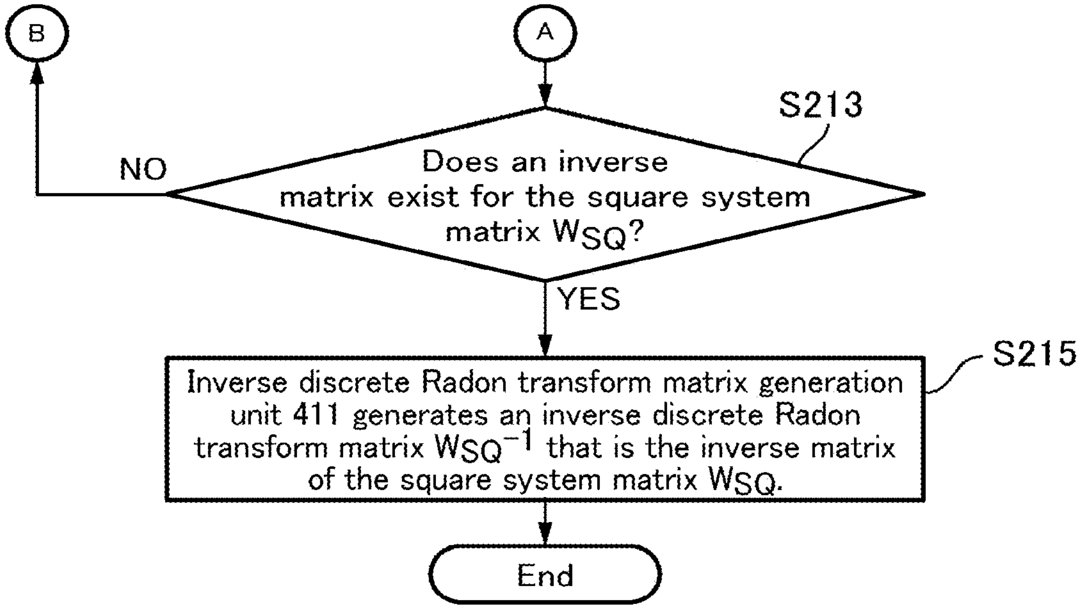
FIG. 12B is a flowchart of an example of an inverse discrete Radon transform matrix generation process according to an embodiment of the present invention.

FIGS. 12A and 12B show a flowchart of an example of an inverse discrete Radon transform matrix generation process according to the present embodiment.

On the basis of the operating parameters obtained by the above operating parameter computing process, or regardless thereof, a user designates three operating parameters, namely a number of detection elements N+j, a number of projections N+k, and a scan angle range φ of less than (180°-180°/number of projections) via the input unit of the inverse discrete Radon transform matrix generation device 40 (S201). The operating parameter value reception unit 403 of the inverse discrete Radon transform matrix generation device 40 receives the values of the designated three operating parameters (S203).

The system matrix determination unit 405 determines a system matrix W on the basis of the designated values of the three operating parameters (S205).

In the same manner as performed in the steps S109 to S111, the square system matrix generation unit 407 generates a square system matrix $W_{SQ}$ by removing, from the determined system matrix W, the elements of predetermined (j+k)×N+j×k row vectors in total, except for the case where j=k=0. For the above, the elements of overlapping row vectors are first removed from the elements of row vectors constituting the determined system matrix W (S207). Next, whether to keep or decimate the elements of the remaining row vectors is randomly determined using numerically-generated random numbers, and the elements of (j+k)×N+j×k row- or column vectors in total are removed to generate a square system matrix $W_{SQ}$ (S209). If the square system matrix generation unit 407 decides that the elements of row vectors constituting the square system matrix $W_{SQ}$ include elements that are the same as those of row vectors removed in the step S207, the square system matrix generation unit 407 stores in the storage unit 413 indexes (row numbers) specifying the rows that correspond to the elements of the row vectors constituting the square system matrix $W_{SQ}$ and the rows that correspond to the elements of the row vectors that are the same as the row vectors removed (S211).

The inverse matrix decision unit 409 decides whether an inverse matrix exists for the generated square system matrix $W_{SQ}$ in the same manner as performed in the step S113 (S213). If the existence of an inverse matrix is decided (S213—Yes), the inverse discrete Radon transform matrix generation unit 411 generates an inverse discrete Radon transform matrix $W_{SQ}^{-1}$ that is the inverse matrix of the square system matrix $W_{SQ}$ (S215). If the existence of no inverse matrix is decided (S213—No), the process returns to the step S209 and generates a square system matrix $W_{SQ}$ on the basis of other random numbers (S217).

<Reconstructed Image Generation Process>

Figure 13A:
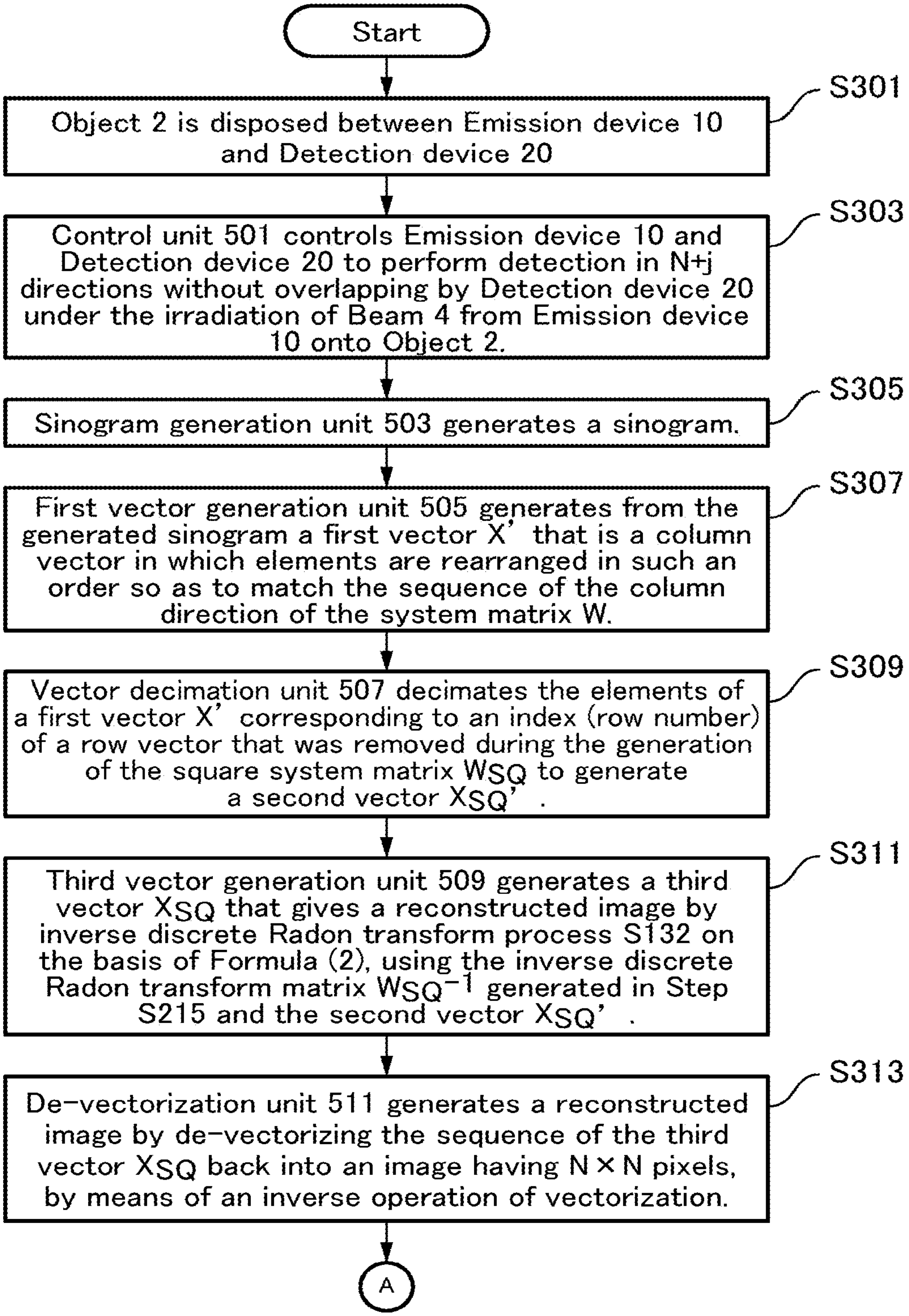
FIG. 13A is a flowchart of an example of a reconstructed image generation process according to an embodiment of the present invention.
Figure 13B:
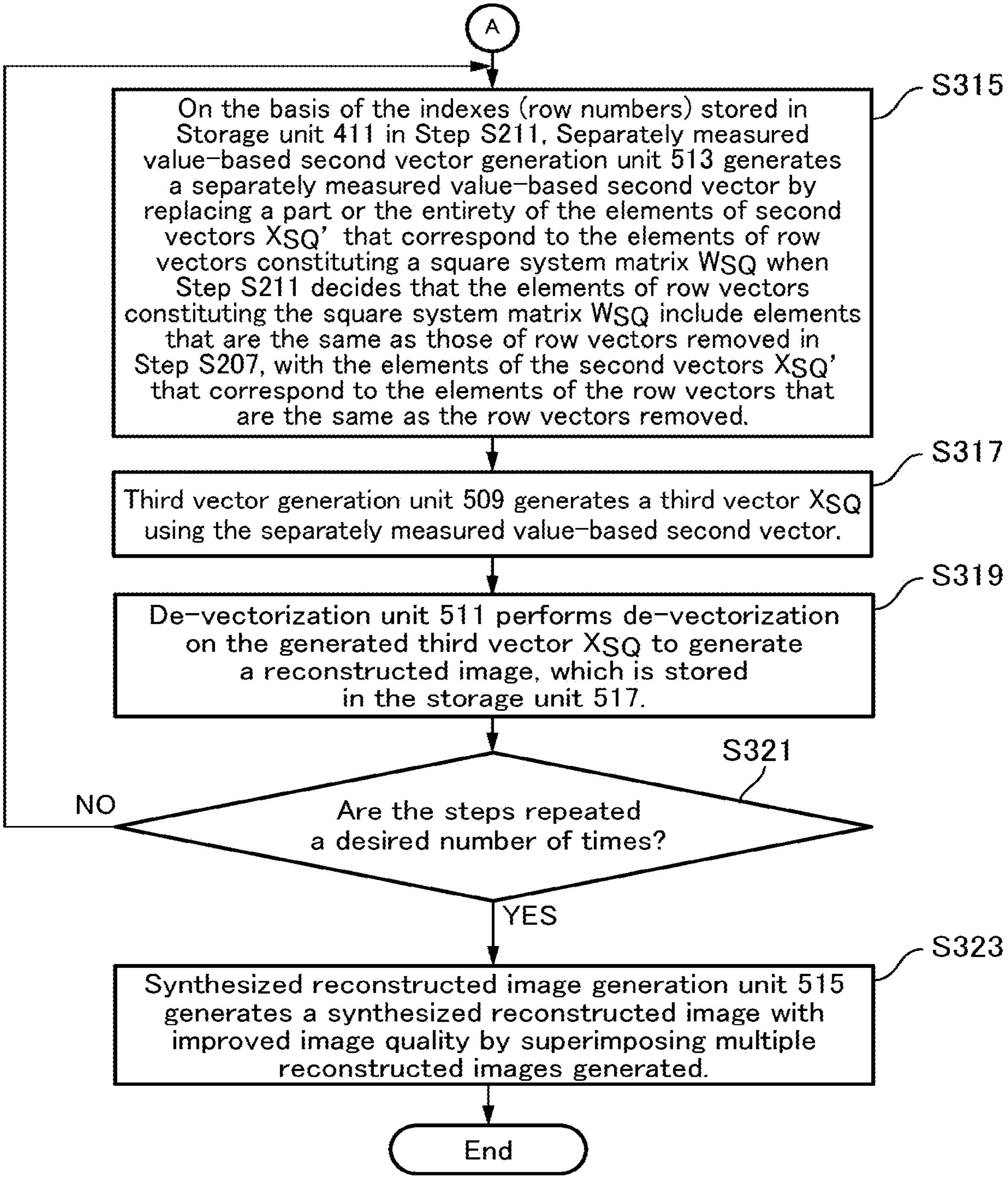
FIG. 13B is a flowchart of an example of a reconstructed image generation process according to an embodiment of the present invention.

FIGS. 13A and 13B show a flowchart of an example of a reconstructed image generation process according to the present embodiment.

The object 2 is disposed between the emission device 10 and the detection device 20 (S301). The control unit 501 of the reconstructed image generation device 50 controls the emission device 10 and the detection device 20 to perform detection in N+j directions without overlapping by the detection device 20 under the irradiation of the beam 4 from the emission device 10 onto the object 2 (S303).

The sinogram generation unit 503 of the reconstructed image generation device 50 generates a sinogram by using the signals obtained from each of the detection elements 22 of the detection device 20, and as necessary, by performing processing such as corrections and scale conversions for the physical characteristics of the instruments, and arranging the sequence order (S305). This process for generating a sinogram is the irradiation and detection process, which is a discrete Radon transform.

The first vector generation unit 505 of the reconstructed image generation device 50 generates from the generated sinogram a first vector X' that is a column vector in which elements are rearranged in such an order so as to match the sequence of the column direction of the system matrix W (S307). Since the first vector X' has a value of a sinogram, it has (N+k)×(N+j) elements. From the irradiation and detection step S301 to the vectorization step S307, quantization by analog-to-digital conversion of the signal and processing of the digital signal and, as necessary, temporary storage of the data can also be done. The display of a sinogram is not necessarily required as long as data that can generate the sinogram are obtained, and reference to explicit data that can be regarded as a sinogram is also unnecessary. Any process that performs any equivalent process from the irradiation and detection step S301 to the vectorization step S307 (for example a simulation process) is also included in the present embodiment as long as a first vector corresponding to the vectorized sinogram is obtained.

The vector decimation unit 507 of the reconstructed image generation device 50 decimates the elements of a first vector X' corresponding to an index (row number) of a row vector that was removed during the generation of a square system matrix $W_{SQ}$ (vector decimation process) to generate a second vector $X_{SQ}'$ (S309). Such a vector decimation process can yield the second vector $X_{SQ}'$ that is a column vector with N×N elements and can satisfy the relationship represented by Formula (4) with the square system matrix $W_{SQ}$.

Since the second vector $X_{SQ}'$ satisfies the relationship represented by Formula (4) with the square system matrix $W_{SQ}$, the relationship represented by Formula (5) holds using an inverse discrete Radon transform matrix $W_{SQ}^{-1}$ which is the inverse matrix of the square system matrix $W_{SQ}$. The third vector generation unit 509 of the reconstructed image generation device 50 generates a third vector $X_{SQ}$ that gives a reconstructed image by an inverse discrete Radon transform process on the basis of Formula (5), using the inverse discrete Radon transform matrix $W_{SQ}^{-1}$ generated in the step S2135 and the second vector $X_{SQ}'$ (S311).

The de-vectorization unit 511 of the reconstructed image generation device 50 generates a reconstructed image by de-vectorizing the sequence of the third vector $X_{SQ}$ back into an image having N×N pixels by means of an inverse operation of vectorization (S313). The tomographic image for one slice is thereby reconstructed.

On the basis of the indexes (row numbers) stored in the storage unit 411 in the step S211, the separately measured value-based second vector generation unit 513 of the reconstructed image generation device 50 generates a separately measured value-based second vector by replacing a part or the entirety of the elements of second vectors $X_{SQ}'$ that correspond to the elements of row vectors constituting a square system matrix $W_{SQ}$ when the step S211 decides that the elements of row vectors constituting the square system matrix $W_{SQ}$ include elements that are the same as those of row vectors removed in the step S207, with the elements of the second vectors $X_{SQ}'$ that correspond to the elements of the row vectors that are the same as the row vectors removed (S315).

The third vector generation unit 509 generates a third vector $X_{SQ}$ using the separately measured value-based second vector (S317). Then, the de-vectorization unit 511 performs de-vectorization on the generated third vector $X_{SQ}$ to generate a reconstructed image, which is stored in the storage unit 517 (S319).

The steps S315 to S319 are repeated a desired number of times on different combinations of row vectors constituting a square system matrix $W_{SQ}$ if the step S211 has decided that the elements of row vectors constituting the square system matrix $W_{SQ}$ include the elements that are the same as those of row vectors removed in the step S207, and the elements of the row vectors that are the same as the row vectors removed (S321). The synthesized reconstructed image generation unit 515 of the reconstructed image generation device 50 generates a synthesized reconstructed image with improved image quality by superimposing multiple reconstructed images generated (S323).

(Verification by Computer Simulation (Examples))

Figure 14:
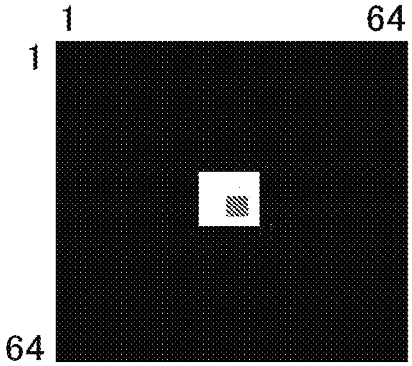
FIG. 14 is a diagram showing verification data (8-bit numerical phantom) used for verification.
Figure 15A:
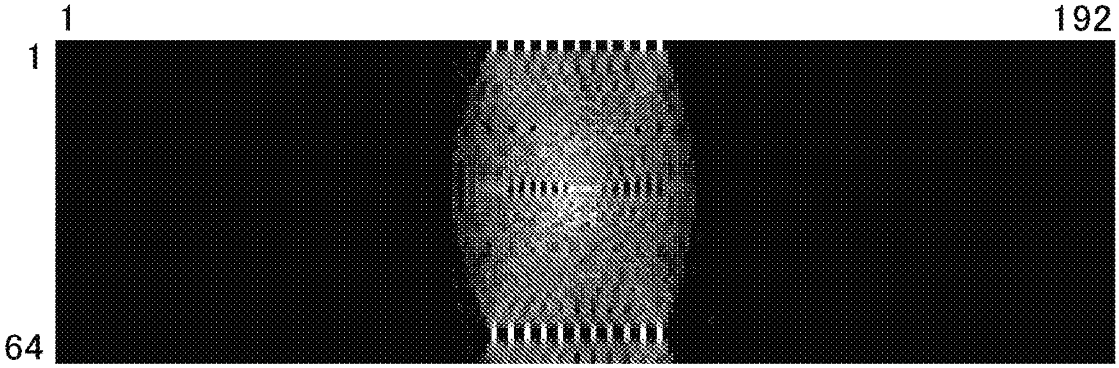
FIG. 15A is a diagram showing an example of a sinogram when a number of detection elements is larger than a resolution.
Figure 16A:
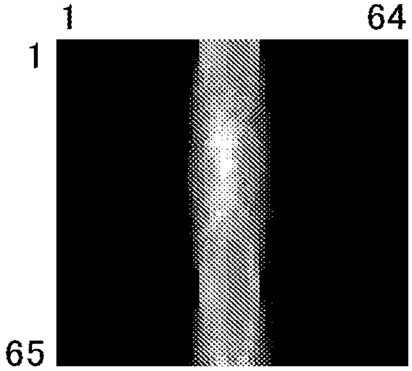
FIG. 16A is a diagram showing an example of a sinogram when a number of projections is larger than a resolution.
Figure 17A:
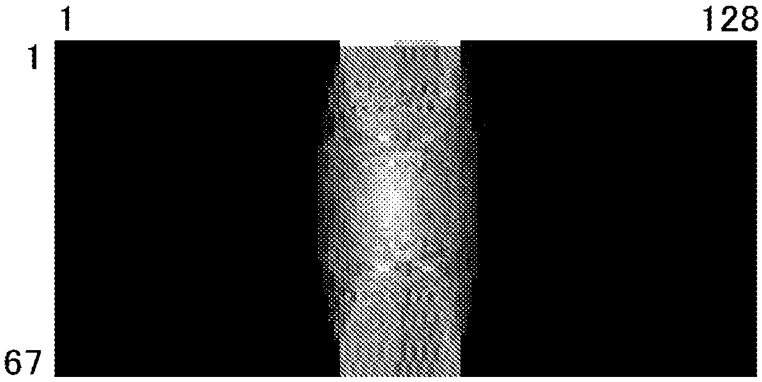
FIG. 17A is a diagram showing an example of a sinogram when numbers of detection elements and projections are larger than a resolution.

The effectiveness of the reconstruction method according to the present embodiment was confirmed by computer simulation. The general processing, including the inverse Radon transform, and also including those of conventional methods for contrast (Comparative Example), was performed using the mathematical processing software Mathematica (Wolfram Research, Inc., Champaign, Illinois) and the image processing software ImageJ (U.S. National Institutes of Health). A computer with an Intel Xeon E5 processor (3.5 GHZ, 6-Core type) CPU and a 64 GB main memory, or a computer with an Apple M1 processor (8-Core type) CPU and a 16 GB main memory were employed for the simulation process in Examples and Comparative Examples, also including simulation of the irradiation, detection, and sinogram generation. FIG. 14 shows verification data (8-bit numerical phantoms) used for verification (referred to as an original image). FIGS. 15A, 16A, and 17A are diagrams showing examples of sinograms corresponding to the aforementioned cases where the number of detection elements is larger than a resolution; the number of projections is larger than a resolution; and the number of detection elements and the number of projections are larger than a resolution, respectively. In each diagram, numerical values indicating the first and last pixel numbers representing the coordinates of the pixels are shown on the top and left-hand sides. The original image (numerical phantom) is numerical data artificially given for simulating the structure of attenuation rate in a cross-section of an object in a computer simulation, and can be expressed as an image having pixels corresponding to spatial positions with a resolution of N. In the present examples, the original image can be expressed as an image having 64×64 pixels (N=64). In FIG. 14, the region of strong absorption is depicted brightly and the region of weak absorption is depicted darkly. In the computer simulation, the operation of the irradiation and detection by the tomographic imaging device 10 was also simulated, and numerical data corresponding to the measured values were obtained by computation. In a sinogram representing the above, the low value of detection intensity is lightened and the high value is darkened. The sinograms in FIGS. 15A, 16A, and 17A were obtained on the basis of the discrete Radon transform, which corresponds to each measurement operation. Specifically, the sinograms were confirmed by the following three patterns:

(1) As an example of a case where the number of detection elements is larger than a resolution, a discrete Radon transform was performed by a detection device 20 having (N+k)=192 detection elements 22 with N=64 and the number of additional detection elements k=128, in a scan angle range of 98.4°, for a projection from (N+j)=64 directions with the number of additional projections j=0 adopted. To reflect this, the sinogram shown in FIG. 15A is displayed as an image with a size of 192×64 pixels.

(2) As an example of a case where the number of projections is larger than a resolution, a discrete Radon transform was performed by a detection device 20 having (N+k)=64 detection elements 22 with N=64 and the number of additional detection elements k=0, in a scan angle range of 118.15°, for a projection from (N+j)=65 directions with the number of additional projections j=1 adopted. To reflect this, the sinogram in FIG. 16A is displayed as an image with a size of 64×65 pixels.

(3) As an example of a case where the number of detection elements and the number of projections are larger than a resolution, a discrete Radon transform was performed by a detection device 20 having (N+k)=128 detection elements 22 with N=64 and the number of additional detection elements k=64, in a scan angle range of 93.3°, for a projection from (N+j)=67 directions with the number of additional projections j=3 adopted. To reflect this, the sinogram in FIG. 17A is displayed as an image with a size of 128×67 pixels.

In the present examples, the addition of the detection elements was performed by reducing the size of the detection elements to maintain the area of a group of detection elements. The sinograms shown in FIGS. 15A, 16A, and 17A are for the operation of the present embodiment, and are also used for the processes of conventional FBP and ML-EM methods. Conventional approaches can obtain a reconstructed image simply by adopting a sinogram obtained in a size of N×N pixels (not shown), particularly requiring neither the addition of detection elements nor the addition of the number of projections. Such a sinogram in a size of N×N pixels, however, has an information volume smaller than that of a sinogram obtained by the present embodiment. For this reason, a sinogram in a size of (N+j)×(N+k) pixels according to the present embodiment is herein adopted to compare approaches on the basis of images reconstructed from sinograms having the same information volume. For the processes of conventional FBP and ML-EM methods, however, a sinogram having an image size reduced by averaging pixel values such that the number of pixels in a detection element direction will be the same as a resolution was used, in order to obtain a reconstructed image having the same size as that of an image obtained in the present examples.

As a verification of the present embodiment, the processes by the above steps S201 to S209, S213 to S215, and S301 to S313 (the steps S301 to S305 perform a computer simulation as described above) were performed for the above three patterns with a number of detection elements (N+j), a number of projections (N+k), and a scan angle range φ as described above to obtain a reconstructed image. The randomized algorithm described above was adopted to determine a decimation sequence {m} in a matrix decimation process. When a process for determining a decimation sequence {m} was actually performed many times on the basis of the above algorithm, the rank sometimes did not match (achieve) N×N (64×64) in the step S213, requiring a retry process of returning to the step S209. The actual rate of retry process required was (1) approximately 1 to 2 retries on average for 10 algorithmic operations when the number of detection elements was larger than a resolution, (2) approximately 35 retries on average for 10 algorithmic operations when the number of projections was larger than a resolution, and (3) approximately 3287 retries on average for 10 algorithmic operations when the number of detection elements and the number of projections are larger than a resolution. The time taken by a computer used in the verification of examples to generate a square matrix satisfying the rank requirement was each (1) approximately 10 to 20 minutes when the number of detection elements was larger than a resolution, (2) approximately 20 to 30 minutes when the number of projections was larger than a resolution, and (3) approximately 8 to 24 hours when the number of detection elements and the number of projections were larger than a resolution. When the addition of the number of projections was as small as approximately one and the measurement angle range was small, the number of rows in total did not significantly increase. However, when a combination of rows was selected therefrom, a matrix did not satisfy the rank requirement even if one dependent row was included therein, and the number of retries for selecting a row satisfying the rank requirement sometimes increased compared with a case of a matrix to which a large number of projections and detection elements were added. This shows that the computation processing time is not determined by the number of rows alone, but it also changes in accordance with the dependency of each row. Since the independency of each row appears to be lowered particularly in a narrow scan angle range, such increase/decrease of the processing time is a behavior that is theoretically assumed.

Figure 15B:
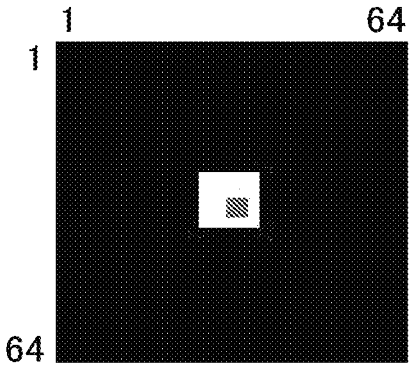
FIG. 15B is a reconstructed image obtained in an example in which a number of detection elements is larger than a resolution.
Figure 15C:
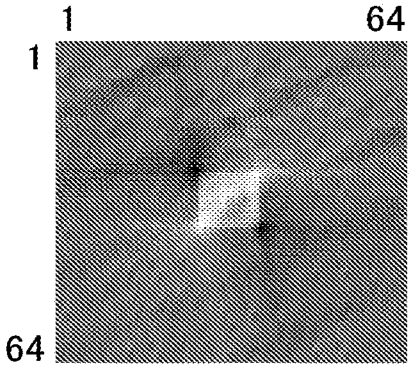
FIG. 15C is a reconstructed image obtained on the basis of the sinogram shown in FIG. 15A, by a conventional FBP method using a Shepp-Logan filter.
Figure 15D:
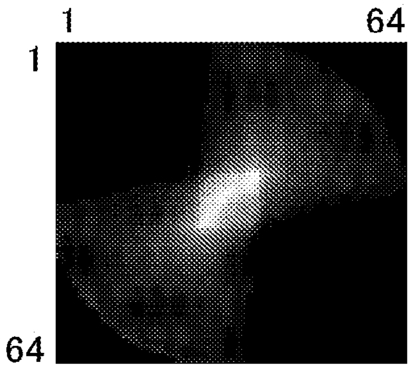
FIG. 15D is a reconstructed image obtained on the basis of the sinogram shown in FIG. 15A, by performing iterative approximation calculation (ML-EM method) 10 times as a conventional algebraic reconstruction method.
Figure 15E:
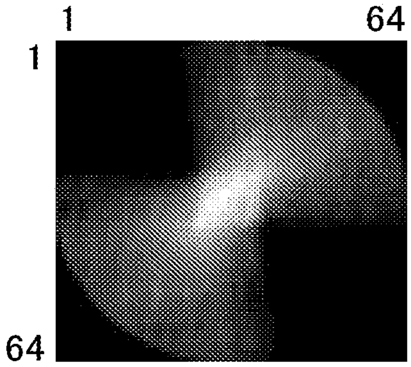
FIG. 15E is a reconstructed image as a reference, obtained on the basis of the sinogram shown in FIG. 15A, by an FBP method using no filter.
Figure 16B:
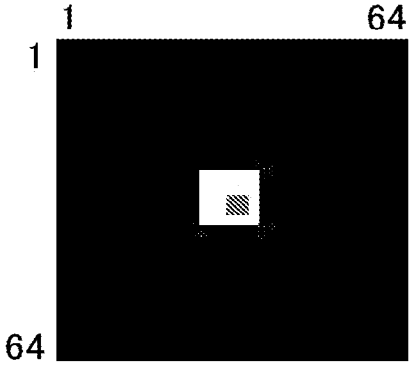
FIG. 16B is a reconstructed image obtained in an example in which a number of projections is larger than a resolution.
Figure 16C:
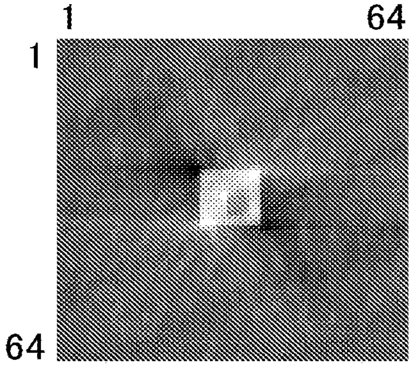
FIG. 16C is a reconstructed image obtained on the basis of the sinogram shown in FIG. 16A, by a conventional FBP method using a Shepp-Logan filter.
Figure 16D:
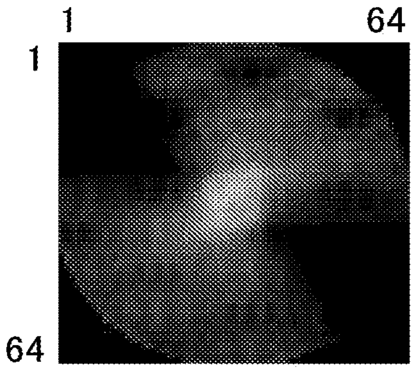
FIG. 16D is a reconstructed image obtained on the basis of the sinogram shown in FIG. 16A, by performing iterative approximation calculation (ML-EM method) 10 times as a conventional algebraic reconstruction method.
Figure 16E:
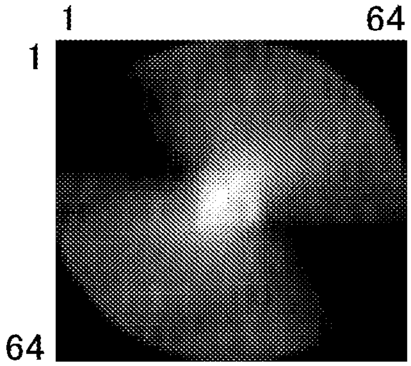
FIG. 16E is a reconstructed image as a reference, obtained on the basis of the sinogram shown in FIG. 16A, by an FBP method using no filter.
Figure 17B:
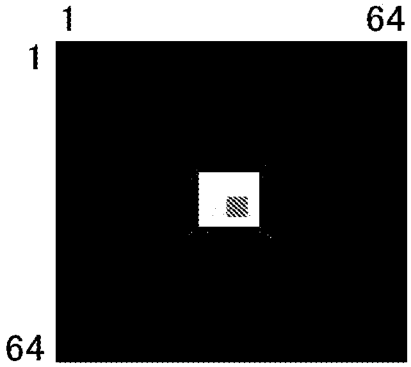
FIG. 17B is a reconstructed image obtained in an example in which numbers of detection elements and projections are larger than a resolution.
Figure 17C:
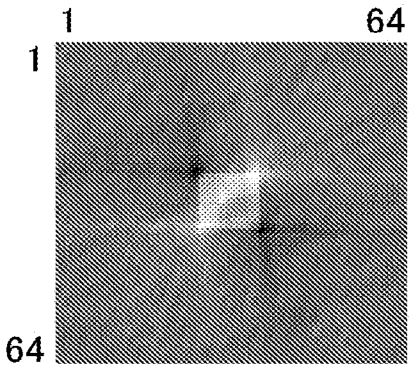
FIG. 17C is a reconstructed image obtained on the basis of the sinogram shown in FIG. 17A, by a conventional FBP method using a Shepp-Logan filter.
Figure 17D:
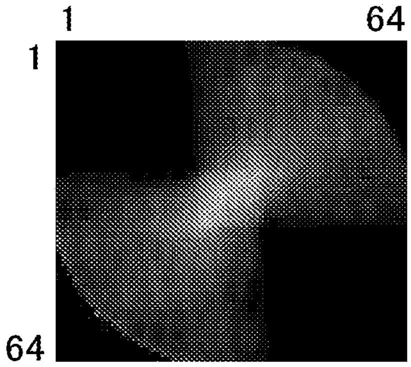
FIG. 17D is a reconstructed image obtained on the basis of the sinogram shown in FIG. 17A, by performing iterative approximation calculation (ML-EM method) 10 times as a conventional algebraic reconstruction method.
Figure 17E:
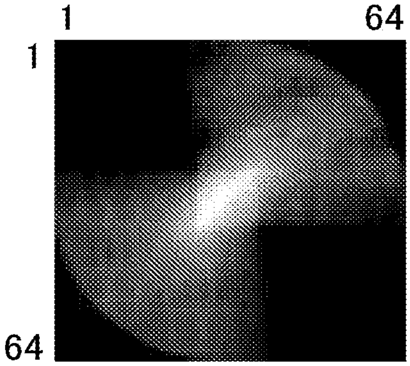
FIG. 17E is a reconstructed image as a reference, obtained on the basis of the sinogram shown in FIG. 17A, by an FBP method using no filter.

FIGS. 15B, 16B, and 17B show reconstructed images obtained in the examples of the above patterns (1), (2), and (3). FIGS. 15C, 16C, and 17C show reconstructed images obtained by a conventional FBP method using a Shepp-Logan filter on the basis of the sinograms shown in FIGS. 15A, 16A, and 17A. FIGS. 15D, 16D, and 17D show reconstructed images obtained on the basis of the sinograms shown in FIGS. 15A, 16A, and 17A by performing iterative approximation calculation (ML-EM method) 10 times in which the local solution is not zero as a conventional algebraic reconstruction method. FIGS. 15E, 16E, and 17E show reconstructed images as references, which were obtained by an FBP method without a filter, on the basis of the sinograms shown in FIGS. 15A, 16A, and 17A.

As is obvious from the comparison between FIGS. 14 and 15B, FIGS. 14 and 16B, and FIGS. 14 and 17B, respectively, a reconstructed image with extremely high reproducibility was obtained in the present embodiment. Particularly, the reconstructed images obtained by the conventional methods exhibited significant impact due to the limited scan angle range, but the reconstructed image of the present embodiment did not exhibit such an impact. Such high reproducibility was similar for any decimation sequences {m} obtained by randomized algorithm with or without retry processing. This is an advantage of the present embodiment, which is supported by the fact that the inverse discrete Radon transform matrix $W_{SQ}^{-1}$ is an algebraic exact solution, unlike the conventional Shepp-Logan-filtered FBP method (cf. FIGS. 15C, 16C and 17C) and the ML-EM method (cf. FIGS. 15D, 16D and 17D). This advantage is also confirmed through the high reproducibility of the images themselves.

Next, a comparison of the reproducibility of the reconstructed images was performed based on a numerical measure. Specifically, the reproducibility of each reconstructed image was evaluated using the ISNR (Improvement in Signal-to-Noise ratio) in Formula (18).

[Math 16] Formula 1

$$ISNR = 10\log_{10}\left(\frac{|\bar{x}-x|^2}{|\hat{x}-x|^2}\right) \tag{18}$$

Here,

[Math 17]

$$x,\ \hat{x},\ \bar{x}$$ Formula 2 are vector representations of the original image shown in FIG. 14, the reconstructed image of either of the target FIGS. 15B to 15D, 16B to 16D, and 17B to 17D, and the reconstructed image of the simple inverse Radon transform (back projection without filters), respectively. The reconstructed images of the simple inverse Radon transform are shown in FIGS. 15E, 16E, and 17E as described above, which are references for comparison. The INSR values of the reconstructed images shown in FIGS. 15B to 15D, 16B to 16D, and 17B to 17D, which were obtained using Formula (18) based on the reconstructed images of the simple inverse Radon transform, are shown in Tables 3, 4 and 5.

TABLE 3

| | Present embodiment (FIG. 15B) | FBP + Shepp-Logan filter (FIG. 15C) | ML-EM (FIG. 15D) |
|---|---|---|---|
| ISNR [dB] | ∞ | −5.8 | 5.5 |

TABLE 4

| | Present embodiment (FIG. 16B) | FBP + Shepp-Logan filter (FIG. 16C) | ML-EM (FIG. 16D) |
|---|---|---|---|
| ISNR [dB] | ∞ | −5.1 | 2.1 |

TABLE 5

| | Present embodiment (FIG. 17B) | FBP + Shepp-Logan filter (FIG. 17C) | ML-EM (FIG. 17D) |
|---|---|---|---|
| ISNR [dB] | ∞ | −6.0 | 2.4 |

Here, since the ISNR values in the present examples were exactly solved for 8-bit data, said values diverged to infinity due to the denominator of zero. It was also numerically confirmed on the basis of each ISNR value that the reproducibility of the reconstructed images according to the present embodiment is significantly increased compared with the reproducibility of the reconstructed images in the conventional examples using the FBP method or the iterative approximation reconstruction method.

In the above, a scan angle range being smaller than the conventionally-expressed "a scan angle range of 180°" is expressed as "a scan angle range of less than (180°-180°/number of projections)" in the present specification and claims. The above embodiment was explained on the assumption that the designated scan angle range was less than (180°-180°/number of projections), but the designated scan angle range may be restricted to any appropriate predetermined value of less than 180° (for example, 170° or less, or 165° or less).

The above embodiment was explained on the assumption that the scan angle range is less than (180°-180°/number of projections). However, if the number of additional detection elements j is one or more and/or the number of additional projections k is one or more, a reconstructed image supported by an algebraic exact solution of an inverse discrete Radon transform can be generated using fewer computational resources even though a scan angle range is 180°.

The above embodiment employed an approach of determining the contribution of the pixel for the beam 4 related to the detection element 22 described with reference to FIG. 1B, as one or zero meaning whether the contribution exists or not. In addition to the approach of using the area of the hatched portion in FIG. 1B as the contribution, other practical approaches may be employed in the present embodiment as well. For example, instead of the area, it is also advantageous to have a weight depending on the length of the sweep, or to adopt Siddon's algorithm, which efficiently evaluates the length of the sweep, to determine the above contribution (Non-Patent Document 3). Furthermore, it is also advantageous to utilize the method of Sunnegardh and Danielson, which is capable of anti-aliasing to achieve a higher image quality (Non-Patent Document 4).

Furthermore, although the above embodiment has been explained by the operation of one example of the tomographic imaging device 100, the present embodiment is not necessarily limited to ones employing the emission device 10. The present embodiment can be similarly applied to other techniques such as SPECT (Single Photon Emission Computed Tomography), in which tomographic imaging of an object is performed without the use of an emission device.

For the present invention, some embodiments have been explained for the purpose of exemplification. However, it may be obvious to the person skilled in the art that the present invention is not limited thereto and various variations and modifications may be made to the embodiments and details without deviation from the scope and spirit of the present invention.

In connection with the above description, following items are further disclosed.

(1)

A computer-implemented method for determining an operating parameter of a tomographic imaging system for reconstructing a tomographic image having N×N pixels by an inverse discrete Radon transform in a scan angle range of less than (180°-180°/number of projections), in which the tomographic imaging system obtains an intensity value for each of detection elements, such that, while irradiation of waves or particles to be detected by a detection device toward the detection device is performed by an emission device to an object disposed in a detection range of the detection device having multiple detection elements arranged in at least one row, or while waves or particles not generated by the emission device are transmitted through each part of the object, a detection operation for obtaining an intensity value for each of the detection elements that is performed by receiving waves or particles transmitted through each part of the object by each of the detection elements, is repeated in a scan angle range, while changing the detection direction over the number of projections directions that are not overlapped with each other in relative detection directions for the waves or particles viewed from the object, the method including:

a step for receiving the values of one or two operating parameters designated from among a number of detection elements, a number of projections, and a scan angle range of less than (180°-180°/number of projections);

a step for determining a system matrix on the basis of the values of the designated one or two operating parameters, and on the basis of a predetermined value for an operating parameter other than the operating parameters corresponding to the values of the designated one or two operating parameters, in which designated or predetermined numbers of detection elements and projections are (N+j) and (N+k) respectively (with the proviso that j and k are integers of 0 or more), the system matrix is a matrix having (N+k)×(N+j) column- or row vectors with N×N elements, each of elements having a weight value indicative of contribution of each pixel in the two-dimensional tomographic image having N×N pigments with respect to a path of a portion of the waves or particles, the portion going toward each of the (N+j) detection elements 22, and the column- or row vectors being arranged in a row or a column direction according to each of the (N+k) detection directions while being associated with the pixels of the two-dimensional tomographic image;

a step for generating a square system matrix by removing the elements of predetermined (j+k)×N+j×k row- or column vectors in total from the determined system matrix, except for the case where j=k=0;

a step for deciding whether an inverse matrix exists for the determined square system matrix; and a step for obtaining the value of an operating parameter corresponding to an operating parameter other than the designated one or two operating parameters for which the inverse matrix of the square system matrix exists, by repeating the step for determining a system matrix, the step for generating a square system matrix, and the step for deciding whether the inverse matrix exists, as necessary, for a different predetermined value of an operating parameter other than the operating parameters corresponding to the values of the designated one or two operating parameters.

(2)

The method described in the item (1), in which the step for generating a square system matrix first removes elements of overlapping row- or column vectors from the determined system matrix, and removes elements of predetermined (j+k)×N+j×k row- or column vectors in total to generate a square system matrix.

(3)

The method described in the item (2), in which the step for generating a square system matrix first removes elements of overlapping row- or column vectors from the determined system matrix, and subsequently removes row- or column vectors randomly for elements of the remaining row- or column vectors to remove elements of predetermined (j+k)×N+j×k row- or column vectors in total, and thereby a square system matrix is generated.

(4)

A program for causing a computer to perform the method described in any one of the items (1) to (3).

(5)

A computer-readable recording medium in which the program described in the item (4) is recorded.

(6)

A device for determining an operating parameter of a tomographic imaging system for reconstructing a tomographic image having N×N pixels by an inverse discrete Radon transform in a scan angle range of less than (180°-180°/number of projections), in which the tomographic imaging system obtains an intensity value for each of detection elements, such that, while irradiation of waves or particles to be detected by a detection device toward the detection device is performed by an emission device to an object disposed in a detection range of the detection device having multiple detection elements arranged in at least one row, or while waves or particles not generated by the emission device are transmitted through each part of the object, a detection operation for obtaining an intensity value for each of the detection elements that is performed by receiving waves or particles transmitted through each part of the object by each of the detection elements, is repeated in a scan angle range, while changing the detection direction over the number of projections directions that are not overlapped with each other in relative detection directions for the waves or particles viewed from the object, the device including:

an operating parameter value reception unit for receiving the values of one or two operating parameters designated from among a number of detection elements, a number of projections, and a scan angle range of less than (180°-180°/number of projections);

a system matrix determination unit for determining a system matrix on the basis of the values of the designated one or two operating parameters, and on the basis of a predetermined value for an operating parameter other than the operating parameters corresponding to the values of the designated one or two operating parameters, in which designated or predetermined numbers of detection elements and projections are (N+j) and (N+k) respectively (with the proviso that j and k are integers of 0 or more), the system matrix is a matrix having (N+k)×(N+j) column- or row vectors with N×N elements, each of elements having a weight value indicative of contribution of each pixel in the two-dimensional tomographic image having N×N pigments with respect to a path of a portion of the waves or particles, the portion going toward each of the (N+j) detection elements 22, and the column- or row vectors being arranged in a row or a column direction according to each of the (N+k) detection directions while being associated with the pixels of the two-dimensional tomographic image;

a square system matrix generation unit for generating a square system matrix by removing the elements of predetermined (j+k)×N+j×k row- or column vectors in total from the determined system matrix, except for the case where j=k=0; and an inverse matrix decision unit for deciding whether an inverse matrix exists for the determined square system matrix, said device repeating the system matrix determination, the square system matrix generation, and the decision on whether the inverse matrix exists, as necessary, for a different predetermined value of an operating parameter other than the operating parameters corresponding to the values of the designated one or two operating parameters to obtain a value of an operating parameter corresponding to an operating parameter other than the designated one or two operating parameters, for which the inverse matrix of the square system matrix exists.

(7)

The device described in the item (6), in which the square system matrix generation unit first removes elements of overlapping row- or column vectors from the determined system matrix, and removes elements of predetermined (j+k)×N+j×k row- or column vectors in total to generate a square system matrix.

(8)

The device described in the item (6), in which the square system matrix generation unit first removes elements of overlapping row- or column vectors from the determined system matrix, and subsequently, removes row- or column vectors randomly for elements of the remaining row- or column vectors to remove the elements of predetermined (j+k)×N+j×k row- or column vectors in total, and thereby a square system matrix is generated.

INDUSTRIAL APPLICABILITY

The present disclosure is applicable to any sort of tomographic imaging approach in which waves or particles emitted to an object, for example, can transmit through the object itself. Examples thereof include an X-ray CT scanner, SPECT (Single Photon Emission Computed Tomography), Optical tomography, Optical CT devices, and Transmission Electron Microtomography (TEMT).

REFERENCE SIGNS LIST

2 Object
4 Beam
100 Tomographic imaging system
10 Emission device
20 Detection device
22 Detection element
30 Operating parameter computing device
301 Operating parameter interpretation unit
303 Operating parameter reception unit
305 System matrix determination unit
307 Square system matrix generation unit
309 Inverse matrix decision unit
311 Inverse matrix decision unit
**30*a*** CPU
**30*b*** RAM

30c ROM
30d External memory
30e Input unit
30d Output unit
30g Communication unit
30h System bus
40 Inverse discrete Radon transform matrix generation device
403 Operating parameter reception unit
405 System matrix determination unit
407 Square system matrix generation unit
409 Inverse matrix decision unit
411 Inverse discrete Radon transform matrix generation unit
413 Storage unit
50 Reconstructed image generation device
501 Control unit
503 Sinogram generation unit
505 First vector generation unit
507 Vector decimation unit
509 Third vector generation unit
511 De-vectorization unit
513 Separately measured value-based second vector generation unit
515 Synthesized reconstructed image generation unit
517 Storage unit

The invention claimed is:

1. A computer-implemented method for determining an operating parameter of a tomographic imaging system for reconstructing a tomographic image, comprising:

a step for determining a system matrix on the basis of the values of one or two operating parameters designated from among a number of detection elements, a number of projections, and a scan angle range of less than (180°-180°/number of projections);

a step for generating a square system matrix from the system matrix;

a step for deciding whether an inverse matrix exists for the square system matrix; and a step for repeating each of said steps as necessary to determine the value of an operating parameter among the number of detection elements, the number of projections, and the scan angle range of less than (180°-180°/number of projections), the operating parameter corresponding to an operating parameter other than the designated one or two operating parameters for which the inverse matrix of the square system matrix exists, wherein the tomographic image is reconstructed by an inverse discrete Radon transform in the scan angle range of less than (180°-180°/number of projections).

2. The method according to claim 1, wherein the step for generating a square system matrix first removes elements of overlapping row- or column vectors from the determined system matrix to generate a square system matrix.

3. The method according to claim 2, wherein the step for generating a square system matrix first removes elements of overlapping row- or column vectors from the determined system matrix, and subsequently removes row- or column vectors randomly for elements of the remaining row- or column vectors to generate a square system matrix.

4. A non-transitory computer-readable recording medium in which a computer program for causing a computer to perform the method according to claim 1 is recorded.

5. A device for determining an operating parameter of a tomographic imaging system for reconstructing a tomographic image, comprising:

at least one processor; and at least one memory storing a program which when executed by the at least one processor causes operations comprising:

determining a system matrix on the basis of the values of one or two operating parameters designated from among a number of detection elements, a number of projections, and a scan angle range of less than (180°-180°/number of projections);

generating a square system matrix from the system matrix; and deciding whether an inverse matrix exists for the square system matrix, repeating, as necessary, the system matrix determination, the square system matrix generation, and the decision on whether the inverse matrix exists, to determine the value of an operating parameter among the number of detection elements, the number of projections, and the scan angle range of less than (180°-180°/number of projections), the operating parameter corresponding to an operating parameter other than the designated one or two operating parameters for which the inverse matrix of the square system matrix exists, wherein the tomographic image is reconstructed by an inverse discrete Radon transform in the scan angle range of less than (180°-180°/number of projections).

6. The device according to claim 5, wherein the operation of generating a square system matrix first removes elements of overlapping row- or column vectors from the determined system matrix to generate a square system matrix.

7. The device according to claim 5, wherein the operation of generating a square system matrix first removes elements of overlapping row- or column vectors from the determined system matrix, and subsequently removes row- or column vectors randomly for the elements of the remaining row- or column vectors to generate a square system matrix.

8. A computer-implemented method for determining an operating parameter of a tomographic imaging system for reconstructing a tomographic image, comprising:

a step for determining a system matrix on the basis of the values of one or two operating parameters designated from among a number of detection elements, a number of projections, and a scan angle range of a predetermined value being less than 180°;

a step for generating a square system matrix from the system matrix;

a step for deciding whether an inverse matrix exists for the square system matrix; and a step for repeating each of said steps as necessary to determine the value of an operating parameter among the number of detection elements, the number of projections, and the scan angle range of less than 180°, the operating parameter corresponding to an operating parameter other than the designated one or two operating parameters for which the inverse matrix of the square system matrix exists, wherein the tomographic image is reconstructed by an inverse discrete Radon transform in the scan angle range of less than 180°.

9. A device for determining an operating parameter of a tomographic imaging system for reconstructing a tomographic image, comprising:

at least one processor; and at least one memory storing a program which when executed by the at least one processor causes operations comprising:

determining a system matrix on the basis of the values of one or two operating parameters designated from among a number of detection elements, a number of projections, and a scan angle range of a predetermined value being less than 180°;

generating a square system matrix from the system matrix; and deciding whether an inverse matrix exists for the square system matrix; and repeating, as necessary, the system matrix determination, the square system matrix generation, and the decision on whether the inverse matrix exists, to determine the value of an operating parameter among the number of detection elements, the number of projections, and the scan angle range of less than 180°, the operating parameter corresponding to an operating parameter other than the designated one or two operating parameters for which the inverse matrix of the square system matrix exists, wherein the tomographic image is reconstructed by an inverse discrete Radon transform in the scan angle range of less than 180°.

* * * * *